(12) United States Patent
McCall

(10) Patent No.: US 7,950,181 B2
(45) Date of Patent: May 31, 2011

(54) APPARATUS AND METHODS FOR PRODUCTION OF BIODIESEL

(75) Inventor: Joe McCall, Atlanta, GA (US)

(73) Assignee: MIP, LLC, Sandy Springs, GA (US)

( * ) Notice: Subject to any disclaimer, the term of this patent is extended or adjusted under 35 U.S.C. 154(b) by 687 days.

(21) Appl. No.: 12/015,638

(22) Filed: Jan. 17, 2008

(65) Prior Publication Data
US 2008/0220515 A1 Sep. 11, 2008

Related U.S. Application Data

(60) Provisional application No. 60/885,361, filed on Jan. 17, 2007.

(51) Int. Cl.
*A01G 7/00* (2006.01)
*C12M 1/00* (2006.01)
*C12M 3/00* (2006.01)

(52) U.S. Cl. ............ 47/1.4; 435/289.1; 435/292.1

(58) Field of Classification Search .......... 435/292.1, 435/289.1; 47/1.4
See application file for complete search history.

(56) References Cited

U.S. PATENT DOCUMENTS

| | | | |
|---|---|---|---|
| 4,055,491 A | 10/1977 | Porath-Furedi | |
| 4,415,509 A | 11/1983 | Toyooka et al. | |
| 4,555,864 A | 12/1985 | Mori | |
| 4,648,690 A | 3/1987 | Ohe | |
| 4,729,068 A | 3/1988 | Ohe | |
| 4,931,291 A * | 6/1990 | Kojima et al. ............ 426/2 | |
| 5,137,828 A | 8/1992 | Robinson et al. | |
| 5,162,051 A * | 11/1992 | Hoeksema ............ 47/1.4 | |
| 5,179,012 A | 1/1993 | Gudin et al. | |
| 5,188,090 A | 2/1993 | Griggs | |
| 5,242,827 A | 9/1993 | Chaumont et al. | |
| 5,385,298 A | 1/1995 | Griggs | |
| 5,741,702 A | 4/1998 | Lorenz | |
| 5,761,229 A * | 6/1998 | Baldwin et al. ............ 372/31 | |
| 5,846,816 A | 12/1998 | Forth | |
| 5,957,122 A | 9/1999 | Griggs | |
| 6,037,170 A | 3/2000 | Sekine | |
| 6,174,720 B1 | 1/2001 | Oxley et al. | |
| 6,287,852 B1 | 9/2001 | Kondo et al. | |
| 6,348,347 B1 | 2/2002 | Hirabayashi et al. | |
| 6,509,188 B1 | 1/2003 | Trosch et al. | |
| 6,579,714 B1 | 6/2003 | Hirabayashi et al. | |
| 6,602,703 B2 | 8/2003 | Dutil | |
| 6,603,069 B1 | 8/2003 | Muhs et al. | |

(Continued)

OTHER PUBLICATIONS

Bayless, D.J. et al., "Enhanced Practical Photsynthetic CO2 Mitigation," no date, pp. 1-14.

(Continued)

*Primary Examiner* — Christina Johnson
*Assistant Examiner* — Robert Warden
(74) *Attorney, Agent, or Firm* — Kilpatrick Townsend & Stockton LLP

(57) ABSTRACT

A photobioreactor includes a cultivation zone configured to contain a liquid culture medium and facilitate growth of a microalgae biomass, a plurality of parallel edge-lit light transmitting devices mounted within the cultivation zone, and a collection zone oriented in relation to the cultivation zone such that at least a portion of the liquid culture medium and microalgae from the cultivation zone may be periodically harvested. Methods for illuminating algae, for dissolving materials into an algae medium, for extracting oil from algae, and for producing biodiesel from algal oil are also provided.

14 Claims, 13 Drawing Sheets

U.S. PATENT DOCUMENTS

| | | |
|---|---|---|
| 6,627,784 B2 | 9/2003 | Hudson et al. |
| 7,056,725 B1 | 6/2006 | Lu |
| 7,682,821 B2 * | 3/2010 | Woods et al. ............. 435/292.1 |
| 2002/0077373 A1 | 6/2002 | Hudson et al. |
| 2003/0073231 A1 * | 4/2003 | Dutil ......................... 435/292.1 |
| 2004/0070842 A1 | 4/2004 | Bierhuizen |
| 2004/0103783 A1 | 6/2004 | Hudson et al. |
| 2004/0232006 A1 | 11/2004 | Kazem |
| 2005/0032032 A1 * | 2/2005 | Pearce et al. ...................... 435/3 |
| 2005/0042129 A1 | 2/2005 | Kazem |
| 2005/0064577 A1 * | 3/2005 | Berzin ........................ 435/266 |
| 2005/0067122 A1 | 3/2005 | Kazem et al. |
| 2005/0087315 A1 | 4/2005 | Donovan et al. |
| 2005/0150618 A1 | 7/2005 | Kazem et al. |
| 2006/0126428 A1 | 6/2006 | Hudson et al. |
| 2006/0260605 A1 | 11/2006 | Connor |
| 2007/0048848 A1 * | 3/2007 | Sears .......................... 435/134 |
| 2007/0048859 A1 * | 3/2007 | Sears ......................... 435/289.1 |
| 2007/0155006 A1 | 7/2007 | Levin |
| 2007/0264708 A1 | 11/2007 | Bayless et al. |
| 2007/0289206 A1 | 12/2007 | Kertz |
| 2008/0268302 A1 * | 10/2008 | McCall ......................... 429/17 |

OTHER PUBLICATIONS

Borhosa, "Microalgal Photobioreactors: Scale up and Optimism," M.J.G.V., 2003, Chapter 7, pp. 115-148.

Bosma, Rourke, "Ultrasound: A new technique to harvest microalgae?" no date, 1 page.

Dutta, Debajyoti et al., Review "Microbial Cell Factories: hydrogen production by cyanobacteria," 2005, pp. 1-11.

Kremer, G. et al., "Practical Photosynthetic Carbon Dioxide Mitigation," Ohio Coal Research Center, no date, 6 pages.

Mudge, L.K. et al., "Catalytic Generation of Methanol Synthesis Gas from Wood," Pacific Northwest Laboratory, Richland, WA, no date, pp. 179-191.

Pulz, O., "Photobioreactors: Production Systems for Phototrophic Microorganisms," Springer-Verlag, 2001, 7 pages.

Sato, Toru, et al., "Invention of outdoor closed type photobioreactor for microalgae," Energy Conservation and Management 47 (2006) 791-799.

USPTO International Search Report and Written Opinion, Oct. 1, 2008, pp. 1-13, PCT/US08/51298.

* cited by examiner

APPARATUS AND METHODS FOR PRODUCTION OF BIODIESEL

CROSS-REFERENCES TO RELATED APPLICATIONS

This application is a nonprovisional of, and claims the benefit of priority from, U.S. Provisional Patent Application No. 60/885,361 filed Jan. 17, 2007, the entire content of which is incorporated herein by reference for all purposes.

BACKGROUND OF THE INVENTION

Embodiments of the present invention involve techniques for generating renewable fuel, and in particular for producing biodiesel from algae.

There is considerable interest in the development of renewable energy sources to replace petroleum-based fuels. It has been discovered that certain algae have a large oil or lipid content, and thus provide a source for the production of biodiesel. In some cases, algae may contain up to 80% oil by weight. However, there is a lack of efficient and cost-effective algal biomass production systems. Open pond technology is often expensive and susceptible to contamination. Current closed photobioreactors using fiber optic light transmission can be prohibitively expensive.

Therefore, a need exists for improved devices and methods for generating biodiesel from algae. Preferably, such techniques would provide sufficient illumination to algae cultures to support growth. Further, these approaches should provide the required nutrients and gases to support algal growth. These techniques should also provide for the removal of oil from algae cultures. At least some of these objectives will be met by embodiments of the present invention.

BRIEF SUMMARY OF THE INVENTION

Biodiesel and other alternative fuels can be produced from algal oil. Advantageously, embodiments of the present invention provide improved algae culture systems and methods. An exemplary photobioreactor includes a cultivation zone, a collection zone, and a heat sink. The photobioreactor can be in operative association with an agitator and an aggregator. Algae cultures can be grown, harvested, and processed to extract algal oil therefrom. Biodiesel can be produced from the algal oil sustainably, affordably, and on a large scale. Closed systems can provide increased efficiency and cost effectiveness, and reduce the opportunity for contamination.

In a first aspect, embodiments of the present invention provide a method for illuminating algae. The method can include concentrating a stream of light, transmitting the concentrated stream of light to a first portion of a diffusing member, diffusing the concentrated stream of light with the diffusing member, radiating the diffused stream of light from a second portion of the diffusing member, and illuminating the algae with the diffused stream of light. In some cases, the diffusing member comprises a diffusing plate having diffuser particles embedded therein. Relatedly, the diffusing member may include an edge-lit acrylic polymer sheet. The stream of light can be concentrated with a tandem compound parabolic concentrator, a linear Fresnel lens, or the like. In another aspect, embodiments of the present invention provide a method of extracting an algal oil from an algae. The method can include placing the algae in a space between a rotor and a housing, generating relative rotational movement between the rotor and the housing so as to agitate the algae, breaking a cell wall of the algae to allow algal oil to release from the algae into a suspension, flocculating the suspension with a standing sonic wave to isolate the algal oil and pulp, and removing the algal oil and pulp from the suspension. In some aspects, the method may include producing a biodiesel fuel from the algal oil. In another aspect, embodiments of the present invention provide a method of introducing carbon dioxide into an algae suspension. The method can include, for example, transferring the algae suspension from a photobioreactor to an agitation device, and introducing carbon dioxide into the algae suspension with the agitation device. Any of a variety of nutrients or gasses can be introduced into an algae suspension using the agitation device.

In another aspect, embodiments of the present invention provide a photobioreactor for growing and processing an algae culture. The photobioreactor can include a cultivation zone configured to contain a liquid culture medium and facilitate growth of a microalgae biomass, a plurality of parallel edge-lit, light emitting devices mounted within the cultivation zone and extending in a first direction. Each light-emitting device can have a light concentration surface to direct light into the light emitting device. The photobioreactor may also include a collection zone oriented in relation to the cultivation zone such that at least a portion of the liquid culture medium and microalgae from the cultivation zone may be periodically harvested. In some cases, the cultivation zone has a rectangular configuration with a first and a second pair of opposite sidewalls. The light-emitting devices may be positioned so as to extend between the first pair of sidewalls at a predetermined spacing. In some cases, each light emitting device further include or be in operative association with at least one cleaning element that runs along an outer surface of the light emitting device, for cleaning the surface of the light emitting device. The cleaning element may include a brushing apparatus, a scraping apparatus, or the like. The light concentrating surface may be a linear Fresnel lens, a compound parabolic concentrator, or the like. The collection zone can have a rectangular configuration with a first and second pair of opposite sidewalls, can be positioned below the cultivation zone, and can have a total volume sufficient to harvest at least half of the volume of the cultivation zone at periodic intervals. In some aspects, the photobioreactor may have a zone for recovering heat from the cultivation zone, and for cooling the same.

In yet another aspect, embodiments of the present invention provide a culture unit for cultivating microalgae. The culture unit can include, for example, a photobioreactor, a hydrodynamic separation zone in fluid communication with the photobioreactor, and a flocculation tank configured so as to receive material from the separation zone for separation of a biofuel from the microalgae biomass. In some aspects, the hydrodynamic separation zone includes a cavitation mixer capable of separating at least a portion of the microalgae biomass and liquid culture medium into a solid phase containing the solid components of the microalgae and at least one liquid phase. A still further aspect of the present invention provides a method for producing a biofuel. The method may include growing an algae in a cultivation zone of a photobioreactor, transferring the algae from the cultivation zone to a collection zone of the photobioreactor, transferring the algae to an agitator, disrupting the algae to release algal oil therefrom, transferring the disrupted algae and algal oil from the agitator to an aggregator, flocculating the disrupted algae and algal oil with the aggregator, allowing the algal oil to separate from the disrupted algae, and collecting the algal oil and converting the algal oil to the biodiesel. In some cases, the process of growing the algae can include concentrating a stream of light, transmitting the concentrated stream of light to a first portion of a diffusing member, diffusing the concentrated stream of light with the diffusing member, radiating the diffused stream of light from a second portion of the diffusing member, and illuminating the algae with the diffused stream of light. In some cases, the process of disrupting the algae can include placing the algae in a space between a rotor and a housing, generating relative rotational movement between the rotor and the housing so as to agitate the algae, and breaking a cell wall of the algae to allow algal oil to release from the algae. The method may also include introducing carbon dioxide into an algae medium with the agitator.

In one aspect, embodiments of the present invention encompass methods for illuminating an algae. Exemplary embodiments include concentrating a stream of light, transmitting the stream of light to an illuminator having a first surface and a second surface opposite the first surface, transmitting the stream of light within the illuminator between the first and second surface to a reflector disposed between the first surface and the second surface, radiating the stream of light through either the first surface or the second surface of the illuminator, and illuminating the algae with the stream of light. In some cases, the stream of light can be concentrated with a light concentrator having an aperture, and the stream of light can be transmitted through the aperture of the light concentrator to the illuminator. Optionally, the stream of light can be concentrated with a parabolic concentrator, such as a compound parabolic concentrator.

In another aspect, embodiments of the present invention include methods of extracting an algal oil from an algae cultivated in a photobioreactor. Exemplary methods include cultivating the algae in a photobioreactor, placing the algae in a space between a rotor and a housing, generating relative rotational movement between the rotor and the housing so as to agitate the algae, breaking a cell wall of the algae to allow algal oil to release from the algae into a suspension, flocculating the suspension with a standing wave to isolate the algal oil from a pulp comprising the cell wall, and removing the algal oil and the pulp from the suspension. In some cases, the rotor is disposed at least partially within the housing in a concentric arrangement, and the step of generating relative rotational movement between the rotor and the housing comprises creating cavitation in the space between the rotor and the housing to agitate the algae.

In a further aspect, embodiments of the present invention include methods of extracting an algal oil from an algae cultivated in a photobioreactor. Exemplary methods include cultivating or growing an algae in a photobioreactor, placing the algae in an agitator, breaking a cell wall of the algae with the agitator to allow algal oil to release from the algae into a suspension, transferring the suspension from the agitator to an aggregation tank, creating a standing sonic wave in the suspension contained within the aggregation tank with a standing sonic wave generator, aggregating a pulp comprising the cell wall at a pressure node formed by the standing sonic wave, and allowing the pulp to settle toward the bottom of the aggregation tank, separate from the algal oil. In some embodiments, methods include removing the algal oil through a first passage disposed toward a top portion of the aggregation tank. Methods may also include removing the pulp through a second passage disposed toward a bottom portion of the aggregation tank.

In yet another aspect, embodiments of the present invention include methods of extracting an algal oil from an algae. Exemplary methods include placing the algae in a space between a rotor and a housing, where the rotor is disposed at least partially within the housing in a concentric arrangement, and generating relative rotational movement between the rotor and the housing so as to create cavitation in the space between the rotor and the housing and agitate the algae. Methods may also include breaking a cell wall of the algae to allow algal oil to release from the algae into a suspension, and transferring the suspension to an aggregation tank, where the suspension includes the algal oil and the cell wall. Further, methods may include creating a standing sonic wave in the suspension with a standing sonic wave generator, aggregating a pulp, which may include the cell wall, at a pressure node, and allowing the pulp to settle toward the bottom of the aggregation tank, separate from the algal oil. Methods may include removing the algal oil through a first passage disposed toward a top portion of the aggregation tank, removing the pulp through a second passage disposed toward a bottom portion of the aggregation tank, transferring a volume comprising at least a portion of the suspension remaining in the aggregation tank to the space between the rotor and the housing, and infusing the volume with carbon dioxide and nutrients via cavitation.

In some aspects, embodiments of the present invention encompass photobioreactors for growing or cultivating a microalgae biomass. An exemplary photobioreactor can include a cultivation zone configured to contain a liquid culture medium and facilitate growth of the microalgae biomass, and a light concentrator mounted above the cultivation zone. The light concentrator can have a light concentration surface that concentrates a stream of light and directs the stream of light toward an illuminator. The illuminator may include a first surface and a second surface opposite the first surface, and a reflector disposed between the first surface and the second surface that reflects the stream of light through the first surface or the second surface of the illuminator so as to illuminate the microalgae biomass. In some cases, a light concentrator may include an aperture, and the light concentration surface may have a parabolic shape. In some cases, a photobioreactor may include one or more cleaning elements that runs along the first surface or the second surface of the illuminator. Optionally, a cleaning element may include a brushing apparatus or a scraping apparatus. In some cases, a light concentrator may include a compound parabolic concentrator. According to some embodiments, a photobioreactor may include a collection zone having a rectangular configuration with a first and second pair of opposite sidewalls. A collection zone may have a total volume sufficient to harvest at least half of the volume of the cultivation zone at periodic intervals. Optionally, a photobioreactor may include a zone for recovering heat from the cultivation zone, and cooling the cultivation zone.

In another aspect, embodiments of the present invention include a culture unit for cultivating microalgae. An exemplary culture unit may include a cultivation zone configured to contain a liquid culture medium and facilitate growth of the microalgae, and a light concentrator mounted above the cultivation zone, where the light concentrator has a light concentration surface that concentrates a stream of light and directs the stream of light toward an illuminator. A culture unit may also include a collection zone in fluid communication with the cultivation zone, a hydrodynamic separation zone in fluid communication with the cultivation zone, and a flocculation tank in fluid communication with the hydrodynamic separation zone. The hydrodynamic separation zone may include a cavitation mixer having a rotor and a housing, where the rotor is disposed at least partially within the housing in a concentric arrangement. Optionally, a cavitation mixer can be configured to separate at least a portion of the microalgae and liquid culture medium into a solid phase containing a solid component of the microalgae and at least one liquid phase. In some cases, a culture unit may include a standing sonic wave generator configured to create a standing sonic wave within the flocculation tank. According to some embodiments, an illuminator may include a first surface and a second surface opposite the first surface. The illuminator may also include a reflector disposed between the first surface and the second surface that reflects the stream of light through the first surface or the second surface of the illuminator so as to illuminate the microalgae. A culture unit may also include an oxygen container in fluid communication with a cultivation zone. For example, a cultivation zone may be coupled with an oxygen container via a port or conduit. Oxygen produced by algae contained in the cultivation zone can be transferred from the cultivation zone, optionally via the port or conduit, to the oxygen container.

For a fuller understanding of the nature and advantages of the present invention, reference should be had to the ensuing detailed description taken in conjunction with the accompanying drawings.

DETAILED DESCRIPTION OF THE INVENTION

Culture systems and methods are provided for improved algal growth and algal oil extraction from algal cultures. These systems and methods are well suited for the large scale production of biodiesel and other renewable fuels.

Figure 1:
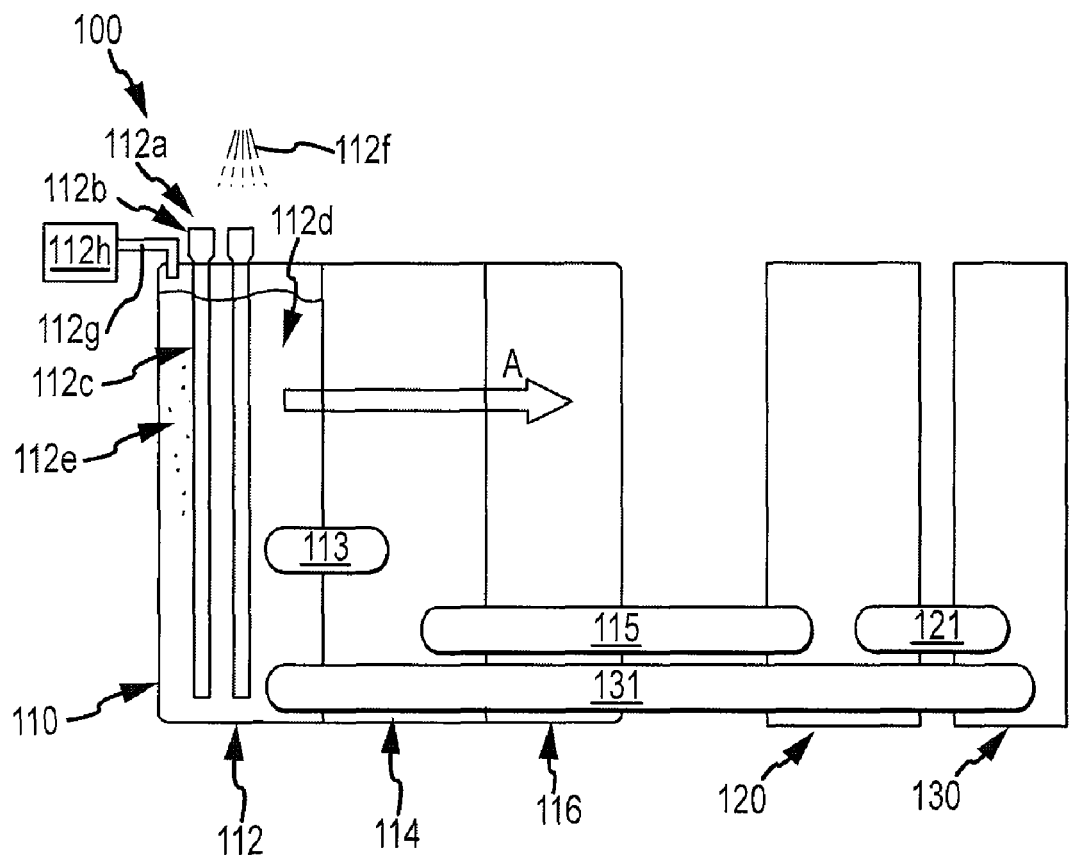
FIG. 1 shows a culture system according to embodiments of the present invention.

Turning now to the drawings, FIG. 1 schematically illustrates a culture system 100 according to embodiments of the present invention. Culture system 100 may include a photobioreactor 110, an agitator 120, and an aggregator or settling tank 130. As shown here, photobioreactor 110 includes a cultivation zone 112, a collection zone 114, and a heat sink 116. Cultivation zone 112 can be in fluid communication with collection zone 114 via a passage or conduit 113. Collection zone 114 can be in fluid communication with agitator 120 via a passage or conduit 115. Agitator 120 can be in fluid communication with aggregator or settling tank 130 via a passage or conduit 121. Similarly, aggregator 130 can be in fluid communication with cultivation zone 112 via a passage or conduit 131. Heat sink 116 can be configured to receive or conduct heat from cultivation zone 112, as indicated by arrow A. In use, an algae culture can be grown or maintained in cultivation zone 112. Typically, cultivation zone 112 provides energy and nutrient requirements sufficient to support or facilitate algae growth, which may include macroalgae or microalgae organisms, such as *Botryococcus braunii* and the like.

In a standard photobioreaction such as photosynthesis, light, water, and carbon dioxide are converted to carbohydrate, lipid, protein, and oxygen. These reactions can be carried out by chloroplasts and chlorophyll in an algae organism. Certain aspects of photobioreactions are discussed in O. Pulz, "Photobioreactors: production systems for phototrophic microorganisms," Appl. Microbiol. Biotechnol. 57(3):287-293 (2001), and in Barbosa et al., "Microalgal photobioreactors: Scale-up and optimization," Chapter 7 pp. 115-148 (2003), the entire contents of each of which are incorporated herein by reference for all purposes. In some embodiments, the dimension of cultivation zone 112, as well as other components of culture system 100, can be optimized for efficient and cost effective manufacturing, shipping, and storage. In some embodiments, one or more components of system 100 may be configured for placement in a cargo container or on a production line.

In some embodiments, cultivation zone 112 includes a light transmission assembly 112a having a light collecting and concentrating means 112b and a light dispersing or distributing means or illuminator 112c. For example, light transmission assembly 112a may include a plurality of parallel edge-lit light dispersing or distributing devices that are mounted within the cultivation zone. Hence, photobioreactor embodiments of the present invention may include a single cultivation zone containing a plurality of light transmission assemblies. The light collecting and concentrating means 112b can have a light concentration surface to direct light into or toward the light diffusing or distributing device or illuminator. In some embodiments, a light concentration surface or collecting and concentrating means 112b can include a linear Fresnel lens, a compound parabolic concentrator, a tandem compound parabolic concentrator, and the like. Sunlight or other ambient light can be collected, concentrated, and transmitted into the dispersing devices or illuminators. Light can then be dispersed, radiated, directed, or distributed into a cultivation medium 112d so as to supply or supplement the light requirements of an algae culture 112e contained within the medium. In use, light transmission assembly can concentrate a stream of light 112f, transmit the concentrated stream of light to a first portion of diffusing member or illuminator 112c, diffuse the concentrated stream of light with the diffusing member, and radiate the diffused stream of light from the diffusing member toward the algae culture so as to illuminate the algae with the diffused stream of light. A photobioreactor or other components of the culture system 100 may also include one or more temperature control means. In some embodiments, cultivation zone 112 may include or be coupled with a port or conduit 112g for transporting oxygen out of the cultivation zone and into an oxygen container 112h.

In some embodiments, cultivation zone 112 has a rectangular configuration with a first and a second pair of opposite sidewalls. For example, a first pair of opposite sidewalls may include a right sidewall and a left sidewall, and a second pair of opposite sidewalls may include a front sidewall and a rear sidewall. Typically, the individual sidewalls of the pair are parallel with each other. Light diffusing devices or illuminators can be positioned so as to extend between the first pair of sidewalls at a predetermined spacing. A light diffusing device or illuminator can include or be in operative association with cleaning element or mechanism for cleaning an outer surface of the light diffusing device. In some cases, a cleaning element may include a brushing apparatus or a scraping apparatus. Additional features of cleaning mechanisms are further discussed below in reference to FIGS. 1A to 1C.

After algae culture 112e has grown as desired, the culture can be transferred via conduit 113 to collection zone 114. An optical testing device can be used to determine whether the density of algae in the cultivation zone has reached a desired level. In some cases, at least a portion of the liquid culture medium and the algae from the cultivation is harvested into the collection zone or harvest tank 114. The collection zone can be positioned below or beneath the cultivation zone. The collection zone can have a total volume sufficient to harvest at least half of the volume of the cultivation zone at periodic intervals. Thus, the harvesting may be performed on a periodic basis. In some cases, unwanted heat may be generated in the photobioreactor, due to the algal growth or heat from the light. For example, if the culture media becomes too hot, the algae may not produce desired levels of oil. If the media becomes too cold, the growth rate of the algae may be slower than desired. Accordingly, system 100 may include a means for regulating temperature in the photobioreactor. Heat sink 116 can act to recover heat from thus cool the cultivation zone. Algae culture and media can then be transferred from collection zone 114 to agitator 120.

Agitator 120, or a portion thereof, may be in fluid communication with collection zone 114 of photobioreactor 110. In some embodiments, agitator 120 includes a hydrodynamic separation zone having a cavitation mixer or a hydrodynamic wheel capable of separating at least a portion of the algae biomass and liquid culture medium into a solid phase containing the solid components of the algae and at least one liquid phase. In use, algae can be placed into a space between a rotor and a housing of agitator 120. By generating relative rotational movement between the rotor and the housing, the agitator 120 can agitate the algae. This agitation can act to break an algal cell wall, and thus algal oil can be released from the algae into a suspension. Contents of agitator 120 can then be transmitted to aggregator 130 via conduit 121. In some embodiments, agitator 120 acts to heat the agitated material. Agitator 120 may include a fluid processing device as described in U.S. Pat. Nos. 5,188,090, 5,385,298, and 5,957,122, all to Griggs, which are incorporated herein by reference. In some cases, agitator 120 may act to mix or integrate carbon dioxide or other gases or nutrients into the media via a cavitation process. In this way, media can be prepared for introduction to the cultivation zone for growth or maintenance of the algae culture. Exemplary mixing devices and techniques are described in U.S. Patent Publication No. 2006/0126428 published Jun. 15, 2006, U.S. Patent Publication No. 2005/0150618 published Jul. 14, 2005, U.S. Patent Publication No. 2005/0067122 published Mar. 31, 2005, U.S. Patent Publication No. 2004/0103783 published Jun. 3, 2004, and U.S. Pat. No. 6,627,784 issued Sep. 30, 2003, all to Hudson et al., the contents of each of which are incorporated herein by reference. Aggregator 130 may include a flocculation tank configured so as to receive material from the separation zone for separation of a biofuel from a microalgae biomass. In some embodiments, one or more culture system components can be preassembled prior to shipping or transporting to an installation site.

Figure 1A:
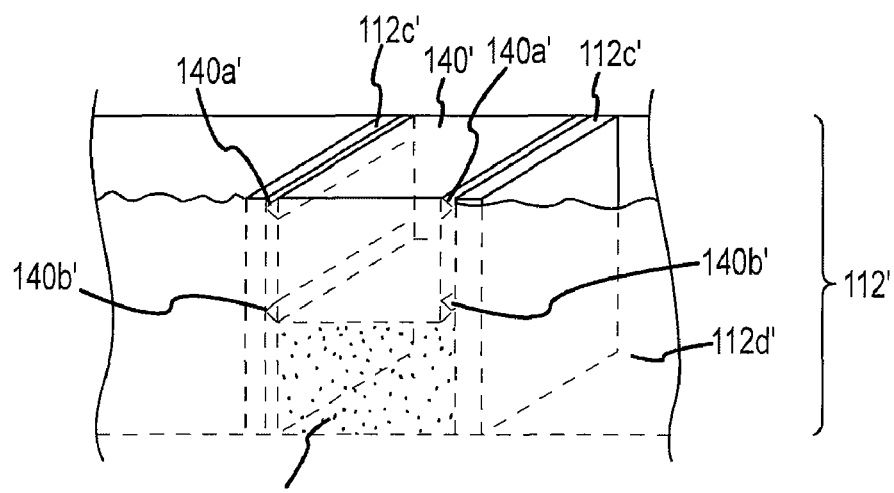
FIGS. 1A to 1C illustrate a cleaning mechanisms according to embodiments of the present invention.
Figure 1B:
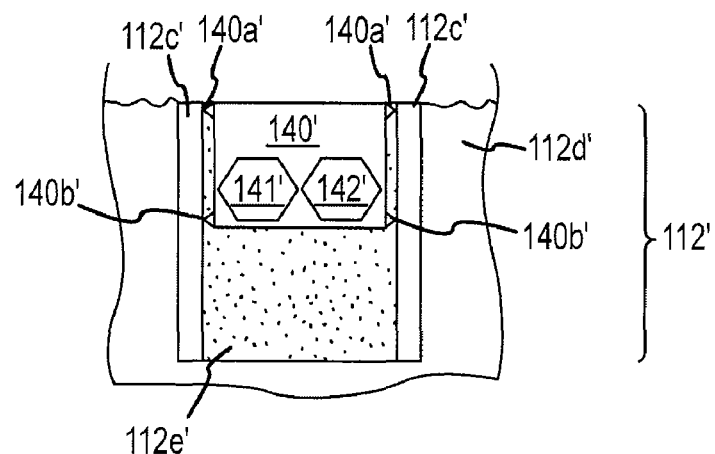
Figure 1C:
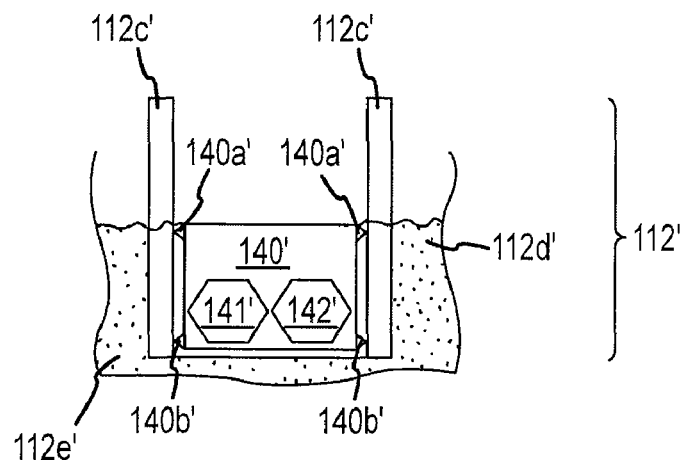

As shown in FIGS. 1A to 1C, a cleaning mechanism 140' may be disposed in a cultivation zone 112' of a photobioreactor. Cleaning mechanism 140' may be constructed of a wire frame, and can include a pair of upper wiping elements 140a' and a pair of lower wiping elements 140b'. As shown in FIG. 1A, cleaning mechanism 140' is floating in a cultivation medium 112d', and is situated between two illuminators 112c'. During the algae growing process, the outer surface of the illuminators may collect various sorts of debris, or portions of the algae culture 112e' may adhere to the illuminator. When material is deposited in this way on the illuminators, the amount of light that passes through the illuminator and into the medium can decrease and thus algae growth can be inhibited. In some embodiments, cleaning mechanism includes or is coupled with a weighting assembly 141', a buoyancy assembly 142', or both, as depicted in FIG. 1B. Weighting assembly 141' and buoyancy assembly 142' can operate to modulate or control the sinking and floating characteristics or operation of cleaning mechanism 140'. In operation, upper wiping elements 140a' act to scrape or scrub debris or algae from the upper one half of illuminators 112c', while lower wiping elements 140b' act to scrape or scrub debris or algae from the lower one half of illuminators 112c'. This scraping or scrubbing action occurs as cleaning mechanism 140' travels between an upper position as shown in FIG. 1B, for example when cultivation zone 112' is completely filled with growth media 112d', and a lower position as shown in FIG. 1C, for example when cultivation zone 112' is half filled with growth media 112d'. In some embodiments, the wiping elements are biased so as to press against the sides of the illuminators. For example, the wiping elements may include a flexible rubber blade or edge that runs along the surface of the illuminator. Similarly, the wiping element may include a spring loaded mechanism that urges a scraping or scrubbing feature of the wiping element against the surface of the illuminator. Exemplary wiping elements may include brushes, blades, scrapers, squeegees, wipers, and the like.

Figure 1D:
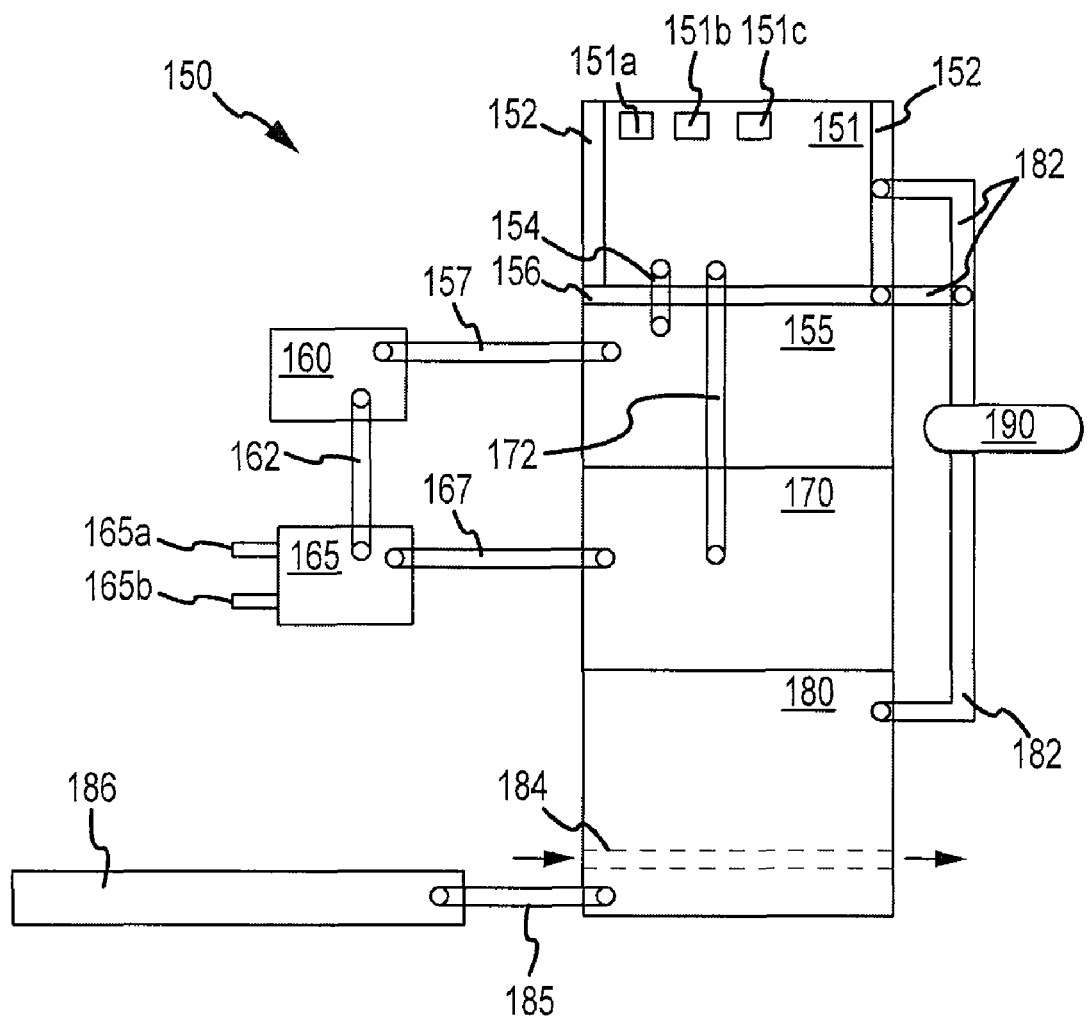
FIG. 1D depicts a culture system according to embodiments of the present invention.

FIG. 1D shows a culture system 150 according to embodiments of the present invention. Culture system 150 includes a photobioreactor having a cultivation zone 151, a collection zone 155, a supplemental collection zone 170, and a heat sink 180. Culture system 150 also includes an agitator 160 and an aggregator 165. Cultivation zone 151, or other components of culture system 150, may include any of a variety of sensors, such as a temperature sensor 151a, a light sensor 151b, or a nutrient or gas sensor 151c. These sensors may be configured to provide culture parameter data to processors or other control mechanisms of the culture system, whereby the operating conditions of the culture system may be controlled or adjusted as desired. As shown here, cultivation zone 151 is in fluid communication with collection zone 155 via conduit 154, collection zone 155 is in fluid communication with agitator 160 via conduit 157, agitator 160 is in fluid communication with aggregator 165 via conduit 162, aggregator 165 is in fluid communication with supplemental collection zone 170 via conduit 167, and supplemental collection zone 170 is in fluid communication with cultivation zone 151 via conduit 172. In some embodiments, agitator 160, aggregator 165, or both, are adjacent to or abut other elements of the culture system, such as the collection zone, the heat sink, or the like. Heat sink 180 is in fluid communication with side panel 152 and bottom panel 156 of cultivation zone 151 via conduit 182. Culture system 150 may include a pump 190 in operative association with conduit 182. In some embodiments, pump 190 may operate to direct fluid from heat sink 180 to one or more panels or heat transfer components of cultivation zone 151. Similarly, pump 190 may operate to direct fluid from one or more panels or heat transfer components of cultivation zone 151 to heat sink 180. Culture system 150 may also include a temperature regulation device 186 in fluid communication with heat sink 180. Temperature regulation device 186 may include a heat dissipation mechanism, a heat collection mechanism, or a combination thereof. In some embodiments, heat sink 180 may include one or more fluid flow tubes or passages 184, which allow ambient or other air or fluid to flow through heat sink 180 and transmit heat to or remove heat from fluid contained in heat sink 180. By providing heat regulation elements such as heat sink 180, temperature regulation device 186, and fluid flow tubes 184, embodiments of the present invention allow for precise and efficient control of heating and cooling of the cultivation zone. The heat regulation features described herein are useful when culture systems are operated in environments that are subject to significant fluctuations in ambient temperature. For example, high desert plains often experience daily and seasonal temperature fluctuations. These heat regulation features can be used to maintain optimal or desired temperatures in the cultivation zone, which may depend on the species of algae or organism cultured, even during extreme temperature swings. Thermal energy from the sun is at least in part due to light in the infrared range, and in some cases a heat regulation feature according to embodiments of the present invention includes a covering that can be placed over the photobioreactor or other component of the culture system. The covering can include selected amounts of infrared absorbing or reflecting material, so as to prevent infrared radiation from reaching the photobioreactor, or otherwise reduce the amount of infrared radiation passing through the covering. This feature may be useful when operating a culture system in a seasonal environment, where it may be desirable to allow the heat-producing infrared radiation to reach the photobioreactor during the cold season, but not to allow the infrared radiation to reach the photobioreactor during the warm season. It is appreciated that components of culture system 150 can be arranged in any horizontal or vertically stacked configuration.

In an exemplary method, algae culture and media are transferred from cultivation zone 151 to collection zone 155, and then are transferred to agitator 160. An agitation procedure shreds the algae and releases oil therefrom, and optionally infuses media with carbon dioxide or other gases or nutrients. Oil, algae pulp, and the like can be transferred from agitator 160 to aggregator 165. The aggregator, which can be or include a flocculation device, operates to separate oil, algae pulp, or both, from the media. Oil can be removed from the aggregator via a first output 165a, and algae pulp can be removed from the aggregator via a second output 165b. Media, optionally infused, can be transferred from aggregator 165 to supplemental collection zone 170, and can remain or be held there until it is transferred to cultivation zone 151.

Figure 1E:
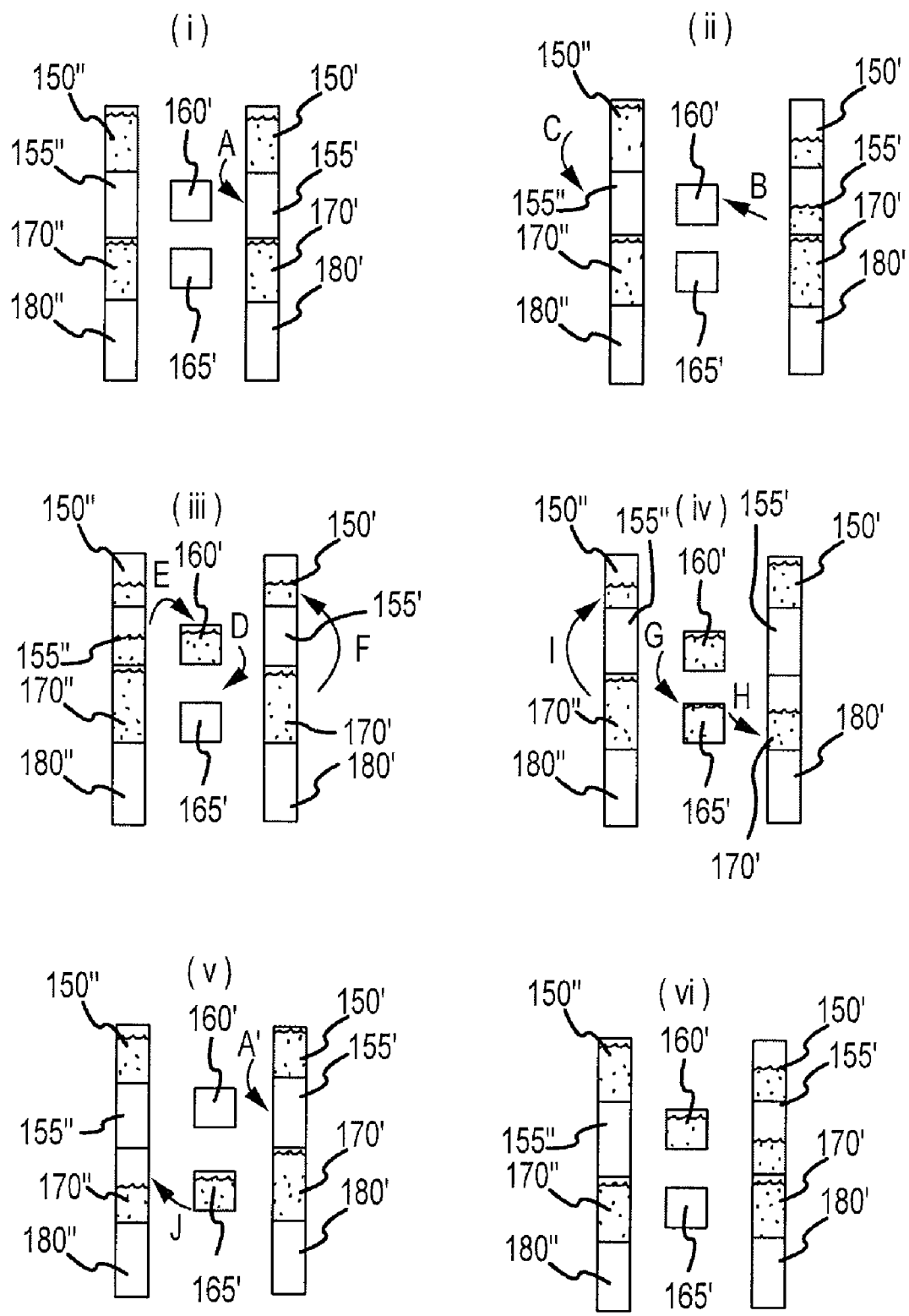
FIG. 1E illustrates aspects of an algae processing method according to embodiments of the present invention.

FIG. 1E provides a schematic representation of an exemplary algae culture processing method according to embodiments of the present invention. With reference to stage (i), a first photobioreactor includes a first cultivation zone 150', a first collection zone 155', a first supplemental collection zone 170', and a first heat sink 180'. In some embodiments, a culture system or culture plant may include one or more photobioreactors. Thus, the culture system depicted in stage (i) includes a second photobioreactor that includes a second cultivation zone 150", a second collection zone 155", a second supplemental collection zone 170", and a second heat sink 180". The culture system also includes an agitator 160' and a settling tank 165'. Stage (i) indicates that cultivations zones 150' and 150" are each full of algae culture and media, and supplemental collection zones 170' and 170" are each full of infused culture media. In a first processing step, as indicated by arrow A, one half of the algae culture and media contained in first cultivation zone 150' is transferred to first collection zone 155'. Stage (ii) indicates that first cultivation zone 150' and first collection zone are each one half full of algae culture and media. In a second processing step, as indicated by arrows B and C respectively, the algae culture and media contained in first collection zone 155' is transferred to agitator 160', and one half of the algae culture and media contained in second cultivation zone 150" is transferred to second collection zone 155". Stage (iii) indicates that agitator 160' contains the algae culture and media that was transferred from first collection zone 155', and second collection zone 155" contains the algae culture and media that was transferred from cultivation zone 150". In a third processing step, the contents of agitator 160' are agitated and then transferred to settling tank 165 as indicated by arrow D, the contents of second collection zone 155" are transferred to agitator 160' as indicated by arrow E, and one half of the infused media from supplemental collection zone 170' is transferred to cultivation zone 150'. Stage (iv) indicates that agitator 160' contains the algae culture and media that was transferred from second collection zone 155", that settling tank 165' contains the shredded algae culture and infused media that was transferred from agitator 160', and that cultivation zone 150' is now full again with algae culture and media. In a fourth processing step, the contents of agitator 160' are agitated and then transferred to settling tank 165' as indicated by arrow G, the contents of settling tank 165' are flocculated and the media is transferred to first supplemental collection zone 170' as indicated by arrow H, and one half of the infused media from second supplemental collection zone 170" is transferred to second cultivation zone 150" as indicated by arrow I. Stage (v) indicates that first supplemental collection zone 170' is full of infused media, that second cultivation zone 150" is full of algae culture and media, that second supplemental collection zone 170" is one half full of infused media, and that settling tank 165' contains the shredded algae culture and infused media that was transferred from agitator 160'. In a fifth processing step, the contents of settling tank 165' are flocculated and the infused media is transferred from settling tank 165' to second supplemental collection zone 170" as indicated by arrow J. The entire process begins again as indicated by arrow A', where one half of the algae culture and growth media contained in first cultivation zone 150' is transferred to first collection zone 155'. The resulting stage (vi) is therefore similar to stage (ii). The present invention contemplates any of a variety of process configurations. For example, in some embodiments, a culture system or plant may have several photobioreactors. Similarly, a culture system having multiple photobioreactors may share common elements such as a common agitator, a common aggregator, a common heat sink, and the like. It is appreciated that the timing or sequence of various processing steps may be controlled or adjusted based on various factors. For example, during the winter there may be less light available to support algal growth, and therefore oil harvesting may occur at a reduced pace. The culture system may carry out a reduced number of production cycles per day, month, or other time period.

Figure 1F:
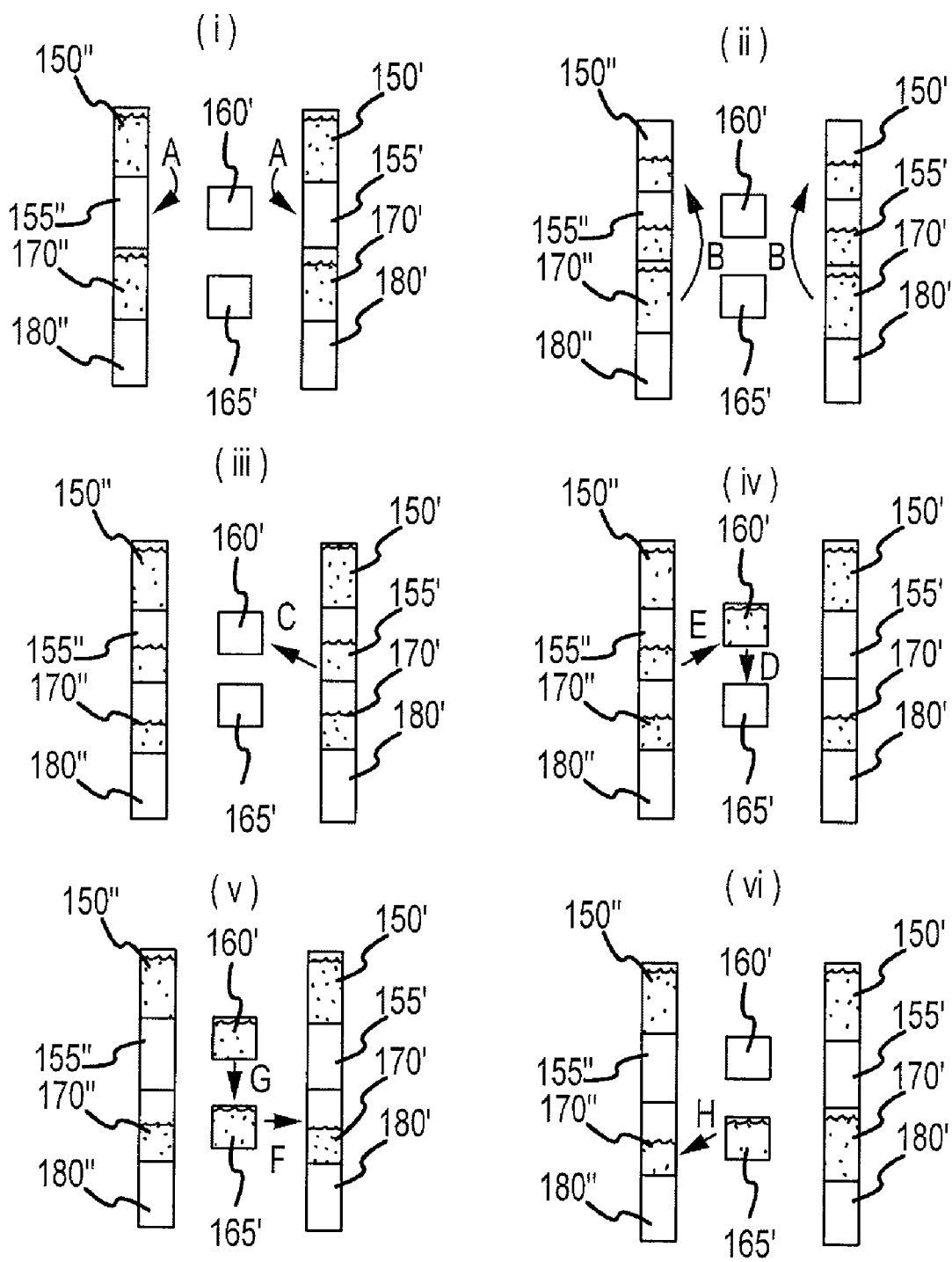
FIG. 1F illustrates aspects of an algae processing method according to embodiments of the present invention.

FIG. 1F provides a schematic representation of an exemplary algae culture processing method according to embodiments of the present invention. With reference to stage (i), a first photobioreactor includes a first cultivation zone 150', a first collection zone 155', a first supplemental collection zone 170', and a first heat sink 180'. In some embodiments, a culture system or culture plant may include one or more photobioreactors. Thus, the culture system depicted in stage (i) includes a second photobioreactor that includes a second cultivation zone 150", a second collection zone 155", a second supplemental collection zone 170", and a second heat sink 180". The culture system also includes an agitator 160' and a settling tank 165'. Stage (i) indicates that cultivations zones 150' and 150" are each full of algae culture and media, and supplemental collection zones 170' and 170" are each full of infused culture media. In a first processing step, as indicated by arrows A, one half of the algae culture and media contained in first cultivation zone 150' is transferred to first collection zone 155', and one half of the algae culture and media contained in second cultivation zone 150" is transferred to second collection zone 155". Stage (ii) indicates that first cultivation zone 150', first collection zone 155', second cultivation zone 150", and second collection zone 155" are each one half full of algae culture and media. In a second processing step, as indicated by arrows B, one half of the infused culture media contained in first supplemental collection zone 170' is transferred to first cultivation zone 150', and one half of the infused culture media contained in first supplemental collection zone 170" is transferred to second cultivation zone 150". By adding infused culture media to the first and second cultivation zones (i.e. stage (ii)) immediately or soon after one half of their contents have been removed (i.e. stage (i)) it is possible to maximize amount of time in the algal growth cycle. Consequently, it is noted that the cultivation tanks are filled in stages (i) and (iii)-(vi). Stage (iii) indicates that first and second cultivation zones 150' and 150" are each filled with original algae culture and media in addition to the newly added infused media. First and second collection zones 155' and 155" are half filled with algae culture and media, and first and second supplemental collection zones 170' and 170" are half filled with infused culture media. As indicated by arrow C, the algae culture and media from first collection zone 155' can be transferred to agitator 160'. Stage (iv) indicates that agitator contains the algae culture and media from first collection zone 155'. As shown by arrow D, after an agitation processing step, the contents of agitator 160' can be transferred to aggregator 165'. Further, as shown by arrow E, the algae culture and media from second collection zone 155" can be transferred to agitator 160'. Stage (v) indicates that agitator 160' contains the algae culture and media from second collection zone 155", and aggregator 165' contains the processed algae culture and media (e.g. shredded algae culture and infused media) from agitator 160'. In a further processing step, the contents of aggregator 165' are flocculated and the infused media is transferred from aggregator 165' to first supplemental collection zone 170' as indicated by arrow F. After an agitation processing step, the contents of agitator 160' can be transferred to aggregator 165' as indicated by arrow G. Stage (vi) indicates that first supplemental collection zone 170' is filled with infused media, and aggregator 165' contains processed algae culture and media from agitator 160'. After an aggregation step, infused media can be transferred from aggregator 165' to second supplemental collection zone 170" as indicated by arrow H. As noted above, the process illustrated in FIG. 1F provides an increased or maximized growing time cycle, as the cultivation zones are filled for a substantial portion of the time. An individual growth cycle can be any desired amount of time, for example 12 hours, 24 hours, and the like. This embodiment allows various procedure steps (e.g. agitation, aggregation) to be carried out while maximum growth occurs in the cultivation zones. In some embodiments, the contents of one or more collection zones can be transferred to the agitator and subsequently processed downstream.

Figure 2:
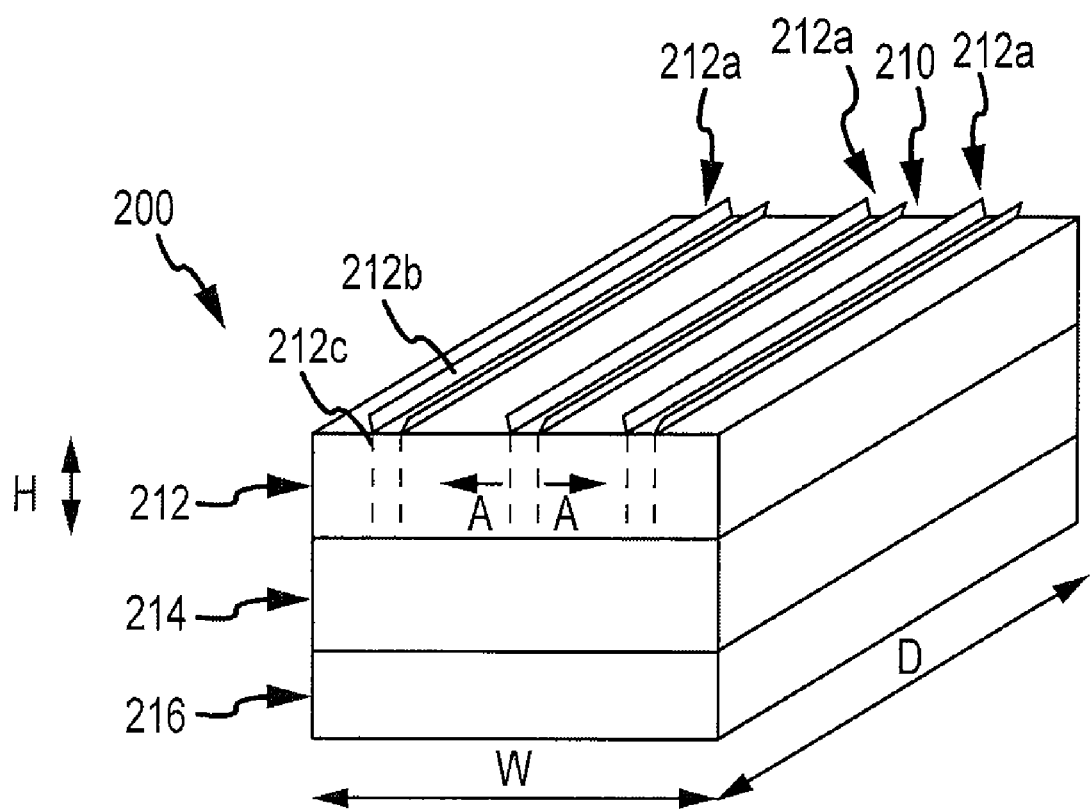
FIG. 2 shows a photobioreactor according to embodiments of the present invention.

FIG. 2 illustrates a photobioreactor 210 of a culture system 200 according to embodiments of the present invention. Photobioreactor 210 includes a cultivation zone 212, a collection zone 214, and a heat sink 216. Cultivation zone 212 can be in fluid communication with collection zone 214. Heat sink 216 can be configured to receive or conduct heat from cultivation zone 212. In use, an algae culture can be grown or maintained in cultivation zone 212. Typically, cultivation zone 212 provides energy and nutrient requirements sufficient to support, facilitate, or optimize algae growth. The cultivation zone as shown in FIG. 2 can have a height H of 3.5', a width W of 40', and a depth D of 11'. An exemplary algae farm may include 100 such photobioreactors in a 10×10 array, such that they occupy about 1 square acre. The cultivation zones, collection zones, and heat sinks may be enclosed with injection molded plastic panels. In some cases, for example, a common side panel may be shared by two adjacent photobioreactors. Cultivation zone 212 may include one or more light transmission assemblies 212a. A light transmission assembly 212a may include a light collecting and concentrating means 212b and a light dispersing or distributing means or illuminator 212c. In some embodiments, light dispersing means or illuminator 212c may be spaced at regular intervals within the cultivation zone. For example, adjacent light dispersing means or illuminators 212c may be separated by a spacing of 16". Light dispersing means or illuminators 212c can radiate light as indicated by arrows A, and thus can illuminate or provide light energy to an algae culture contained in cultivation zone 212.

Figure 2A:
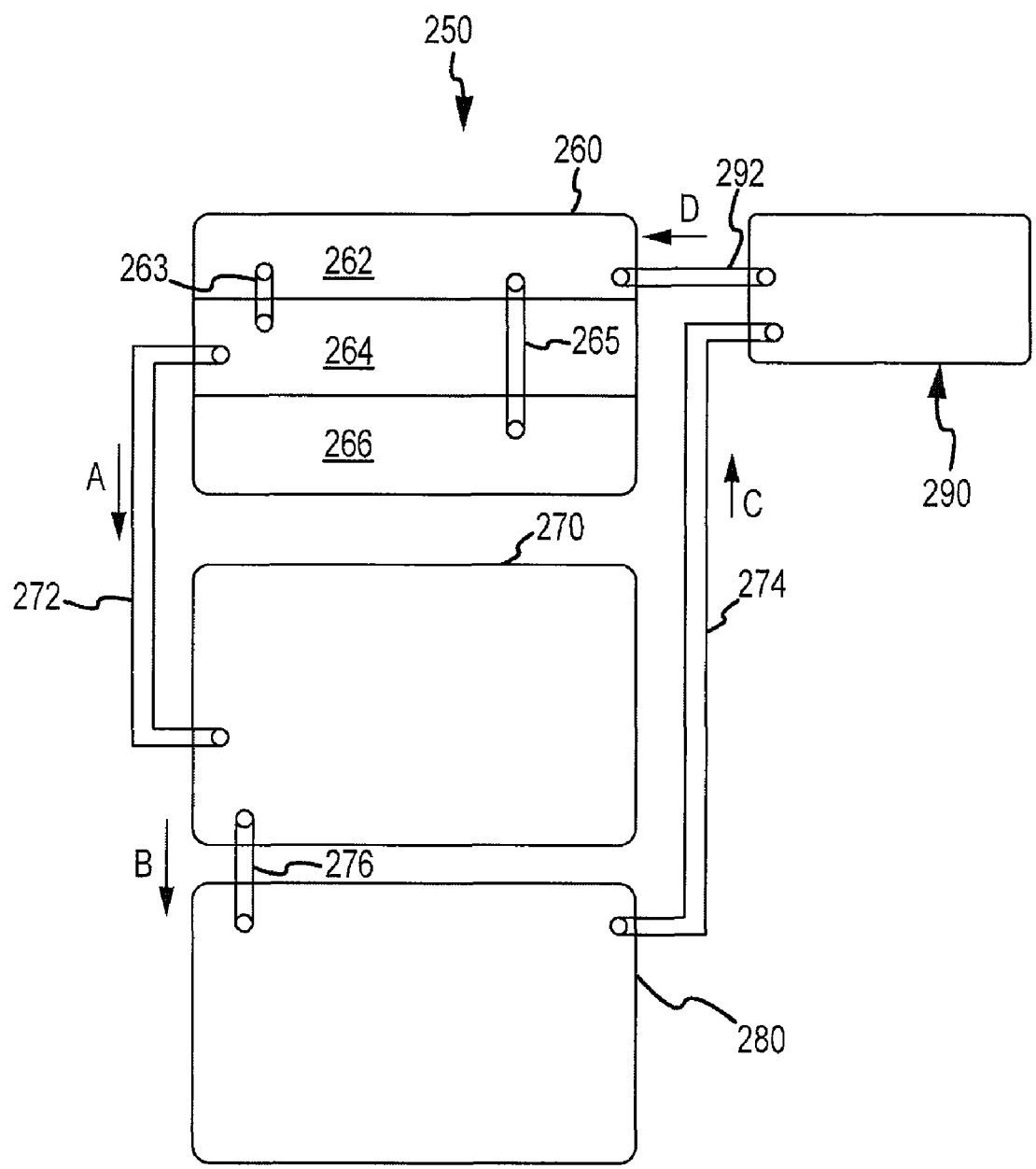
FIG. 2A shows a culture system according to embodiments of the present invention.
Figure 2B:
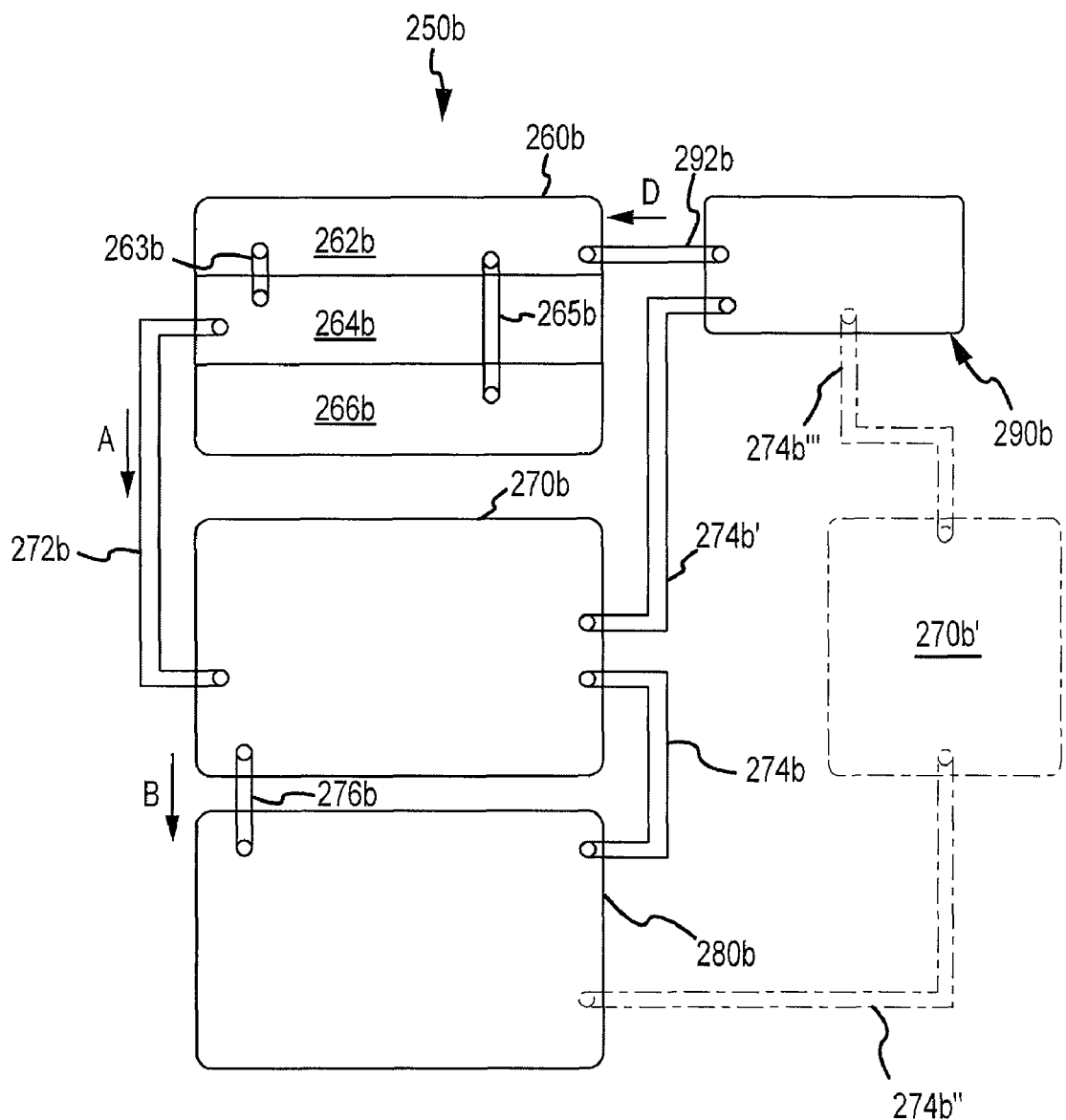
FIG. 2B shows a culture system according to embodiments of the present invention.

FIG. 2A shows a culture system 250 according to embodiments of the present invention. Here, culture system 250 includes a photobioreactor 260, an agitator 270, an aggregator 280, and a supplemental collection zone or tank 290, which may or may not be coupled with or stacked against or between tanks or zones of the photobioreactor. Supplemental collection zone 290 can be used for a variety of purposes. For example, zone 290 may hold liquid media or water following a harvesting step, for recycling materials to a cultivation zone, for receiving materials from an agitator or an aggregator, and the like. In an exemplary method, algae culture and media are transferred from cultivation zone 262 to collection zone 264 through conduit 263, and then are transferred to agitator 270 through conduit 272, as indicated by arrow A. Following an agitation procedure which separates or releases oil from the algae and optionally infuses media with carbon dioxide or other gases or nutrients, the shredded algae and infused media contents are transferred from agitator 270 to aggregator 280 via conduit 276, as indicated by arrow B. The shredded algae culture and media can then be flocculated in aggregator or flocculation tank 280 such that oil is separated from the media, and algae pulp is aggregated. Media can be transferred from aggregator 280 to supplemental collection zone 290 via conduit 274 as indicated by arrow C. Media can remain in supplemental collection zone 290 as desired, and then can be transferred to cultivation zone 262 via conduit 292 as indicated by arrow D. A heat sink 266 can transfer heat to or draw heat from cultivation zone 262 via conduit 265. As depicted in FIG. 2B, in some cases shredded algae culture and media can be transferred from agitator 270b to aggregator 280b, where the shredded algae culture and media can be processed to separate oil and pulp from the media. Further, media can be returned to agitator 270b, or optionally transferred to a second agitator 270b', where the media can be infused with carbon dioxide or other gases or nutrients. The infused media can then be transferred from agitator 270b or 270b' to supplemental collection zone 290b or cultivation zone 262b via any suitable conduit configuration. For example, media can be transferred from aggregator 280b to agitator 270b via a conduit 274b, from agitator 270b to supplemental collection zone 290b via a conduit 274b', from aggregator 280b to agitator 270b' via a conduit 274b", or from agitator 270b' to supplemental collection zone 290b via a conduit 274b'''.

Culture system 250b includes a photobioreactor 260b, an agitator 270b, an aggregator 280b, and a supplemental collection zone or tank 290b, which may or may not be coupled with or stacked against or between tanks or zones of the photobioreactor. Supplemental collection zone 290b can be used for a variety of purposes. For example, zone 290b may hold liquid media or water following a harvesting step, for recycling materials to a cultivation zone, for receiving materials from an agitator or an aggregator, and the like. In an exemplary method, algae culture and media are transferred from cultivation zone 262b to collection zone 264b through conduit 163b, and then are transferred to agitator 270b through conduit 272b, as indicated by arrow A. Following an agitation procedure which separates or releases oil from the algae and optionally infuses media with carbon dioxide or other gases or nutrients, the shredded algae and infused media contents are transferred from agitator 270b to aggregator 280b via conduit 276b, as indicated by arrow B. The shredded algae culture and media can then be flocculated in aggregator or flocculation tank 280b such that oil is separated from the media, and algae pulp is aggregated. Media can be transferred from aggregator 280b to supplemental collection zone 290b. Media can remain in supplemental collection zone 290b as desired, and then can be transferred to cultivation zone 262b via conduit 292b as indicated by arrow D. A heat sink 266b can transfer heat to or draw heat from cultivation zone 262b via conduit 265b.

Figure 3:
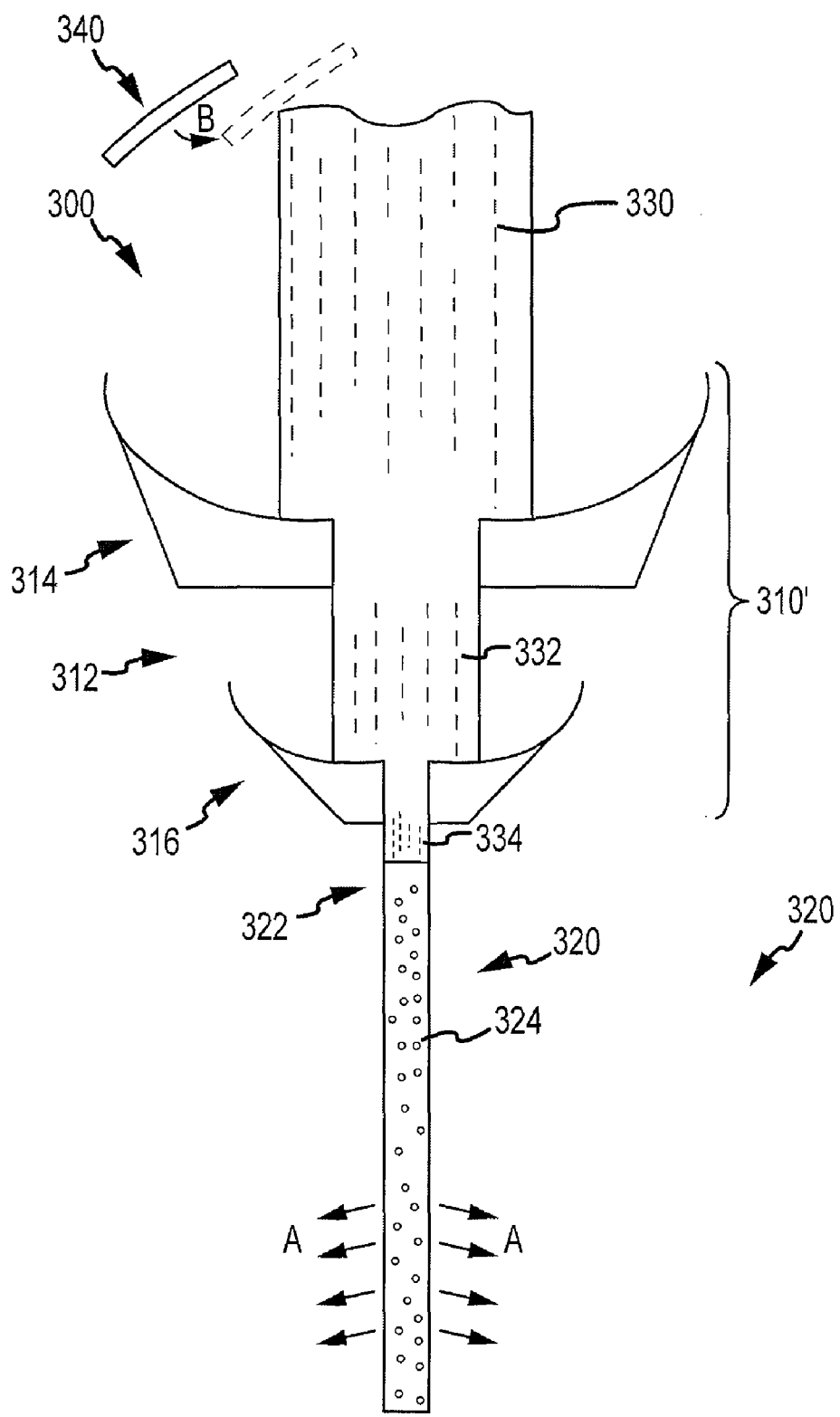
FIG. 3 shows a light transmission assembly according to embodiments of the present invention.

FIG. 3 depicts a light transmission assembly 300 of a culture system according to embodiments of the present invention. Light transmission assembly 300 may include a light collecting and concentrating means 310 and a light dispersing or distributing means or illuminator 320. The light collecting and concentrating means 310 can have one or more light concentration surfaces that aid in directing light into or toward the light diffusing device or illuminator. Sunlight or other ambient light can be collected, concentrated, and transmitted into the dispersing device or illuminator 320. In some embodiments, a light concentration surface or collecting and concentrating means 310 can include a linear Fresnel lens, a compound parabolic concentrator, a tandem compound parabolic concentrator, and the like. The light transmission assembly shown in FIG. 3 includes a tandem compound parabolic concentrator 312 that includes a first compound parabolic concentrator 314 and a second compound parabolic concentrator 316. A parabolic concentrator can include curved or parabolic shaped reflective or mirrored surfaces that face toward each other or otherwise operate to reflect or direct light toward a common point or area. Typically, first compound parabolic concentrator is disposed closer to the sun or other light source. First compound parabolic concentrator 314 may be adapted to collect a light beam having a diameter of about 16 inches. First compound parabolic concentrator 314 may be separated from second compound parabolic concentrator 316 by about 6 inches. In some embodiments, such a concentrator may resemble a trough. Scaffolding (not shown) may hold or secure components of the light transmission assembly in place.

In use, light transmission assembly can focus or concentrate a stream of light 330 into a focused or concentrated stream of light 332, and then into a further focused or concentrated stream of light 334, which is then transmitted to a first portion 322 of light dispersing means or illuminator 320. In some embodiments, concentrated steam of light 334 has a width of about 8 to 10 mm, and correspondingly, diffusing member or illuminator 320 has a width of about 8 to 10 mm. The stream of light can be diffused or distributed in light dispersing means or illuminator 320. In some cases, the light dispersing means or diffusing member 320 includes a diffusing plate having diffuser or reflector particles 324 embedded therein. Optionally, light distributing means or illuminator includes a reflector disposed between a first surface 322a of the illuminator, and a second surface 322b of the illuminator that opposes the first surface. After passing through diffusing member or illuminator 320, the stream of light is radiated from the diffusing member or illuminator, as indicated by arrows A. Diffusing member or illuminator 320 may include a Plexiglas® panel or an Acrylite® Endlighten acrylic sheet (e.g available from CYRO Industries, Rockaway N.J.). In some embodiments, diffusing member or illuminator 320 includes an edge-lit acrylic polymer sheet. Relatedly, diffusing member 320 can include a Plexiglas® acrylic sheet using edge-lit technology (ELiT). Such products can be made by extrusion or casting. In some embodiments, diffusing member or illuminator 320 can provide uniform illumination throughout the member, and can also provide about 92% light transmission. In some embodiments, diffusing member or illuminator 320 can provide nonuniform illumination throughout the member. Often, diffusing member or illuminator 320 includes an additive that scatters light that is introduced at its edges, so that the light diffuses evenly or otherwise as desired through the surfaces of the diffusing member. Thus, when light is focused on the edge of the sheet, the light can be transmitted and evenly diffused to both faces of the sheet. Advantageously, diffusing member or dispersing device 320 allows light energy to be distributed to lower or subsurface levels of a cultivation zone, where algae may otherwise not receive sufficient light energy to sustain growth or maintenance.

In some embodiments, light transmission assembly 300 may include one or more covers or films 340 that can be moved as shown by arrow B so as to block or filter at least a portion of the stream of light 330. Such covers or films can be used to modulate the amount of light entering the collecting and concentrating means 310. Such features may be useful in maintaining optimum or desired growing conditions within the photobioreactor. For example, if an excessive amount of light enters the growth media, the algae may be prompted to form a thick mat. In some embodiments, a cover or film may be transparent. These elements may also be used to protect light transmission assembly components that may otherwise be damaged by hail, wind, and the like. Covers 340 or other light transmission assembly components may also include means for absorbing or filtering light of certain wavelengths, or for modulating the intensity of light that is transmitted through the assembly. For example, diffusing member 320 or cover 340 may include a radiative selective coating or material that blocks, reflects, or filters light of a certain wavelength, while allowing light of another wavelength to pass therethrough. This feature can be used to facilitate or inhibit the growth of algae strains that are responsive to wavelength-specific radiation. In some cases, it may be desired to prevent excessive infrared light from entering the cultivation zone, as such light may generate unwanted heat. Thus, for example, diffusing member 320 or cover 340 may include a material that reflects infrared light and at the same time transmits light that promotes algae growth.

Figure 3A:
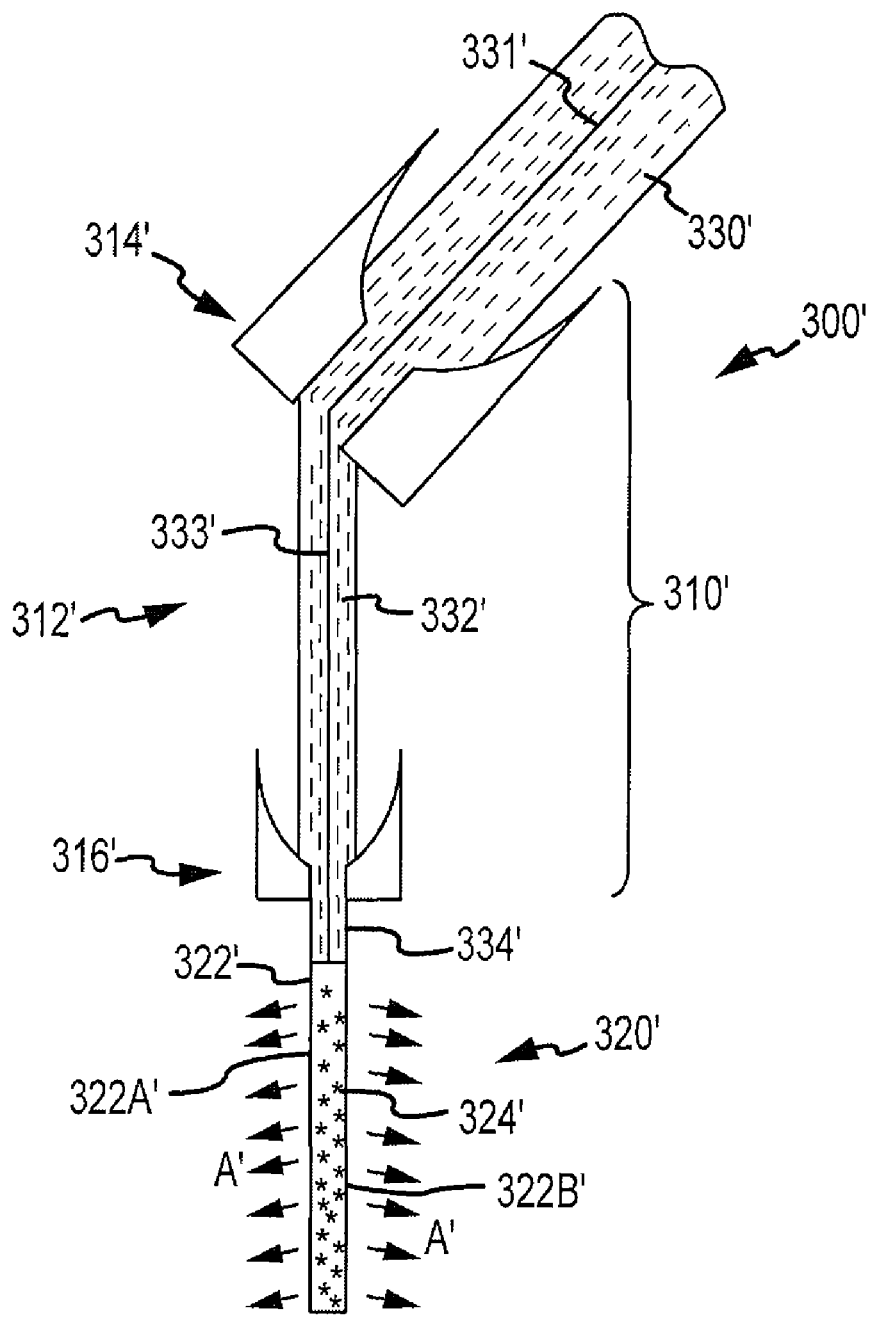
FIG. 3A depicts a light transmission assembly according to embodiments of the present invention.

FIG. 3A depicts a light transmission assembly 300' of a culture system according to embodiments of the present invention. Light transmission assembly 300' may include a light collecting and concentrating means 310' and a light dispersing or distributing means or illuminator 320'. The light collecting and concentrating means 310' can have one or more light concentration surfaces that aid in directing light into or toward the light diffusing device or illuminator. Sunlight or other ambient light can be collected, concentrated, and transmitted into the dispersing device 320'. In some embodiments, a light concentration surface or collecting and concentrating means 310' can include a linear Fresnel lens, a compound parabolic concentrator, a tandem compound parabolic concentrator, and the like. Hence, a light concentration surface may have a parabolic shape. As shown in FIG. 3A, light transmission assembly 300' can direct light along a first axis 331' and a second axis 333', where the first axis is not collinear with the second axis. For example, in some situations it may be desirable to collect light from a certain direction as indicated by axis 331' and then redirect the light in a second direction as indicated by axis 333'. For example, by providing a first compound parabolic concentrator 314' having such a tilt, it may be possible to eliminate the need for a tracking mechanism. However it is appreciated that in some embodiments, the light transmission assembly includes a tracking mechanism that allows the concentrator to align with the light source, which is often the sun. The light transmission assembly may also include motor controls that adjust the angle of tilt in one or more elements of the concentrator 312', which can modulate the amount of light being concentrated.

Figure 3B:
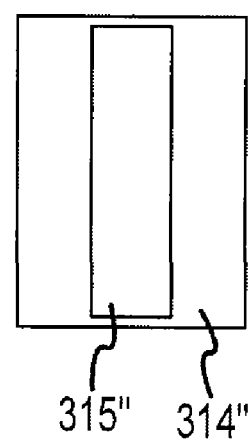
FIG. 3B illustrates a compound parabolic concentrator according to embodiments of the present invention.

The light transmission assembly shown in FIG. 3A includes a tandem compound parabolic concentrator 312' that includes a first compound parabolic concentrator 314' and a second compound parabolic concentrator 316'. In use, light transmission assembly can focus or concentrate a stream of light 330' into a focused or concentrated stream of light 332', and then into a further focused or concentrated stream of light 334', which is then transmitted to a first portion 322' of light dispersing means or illuminator 320'. In some cases, the light dispersing means or diffusing member 320' includes a diffusing plate having diffuser or reflector particles 324' embedded therein. Optionally, the light distributing means or illuminator includes a reflector disposed between a first surface 322a' of the illuminator, and a second surface 322b' of the illuminator that opposes the first surface. After passing through diffusing member or illuminator 320', the stream of light is radiated from the diffusing or distributing member, as indicated by arrows A'. FIG. 3B illustrates a top view of a compound parabolic concentrator 314" according to embodiments of the present invention. As shown here, a trough-like compound parabolic concentrator 314" includes a long rectangular aperture 315".

Figure 4:
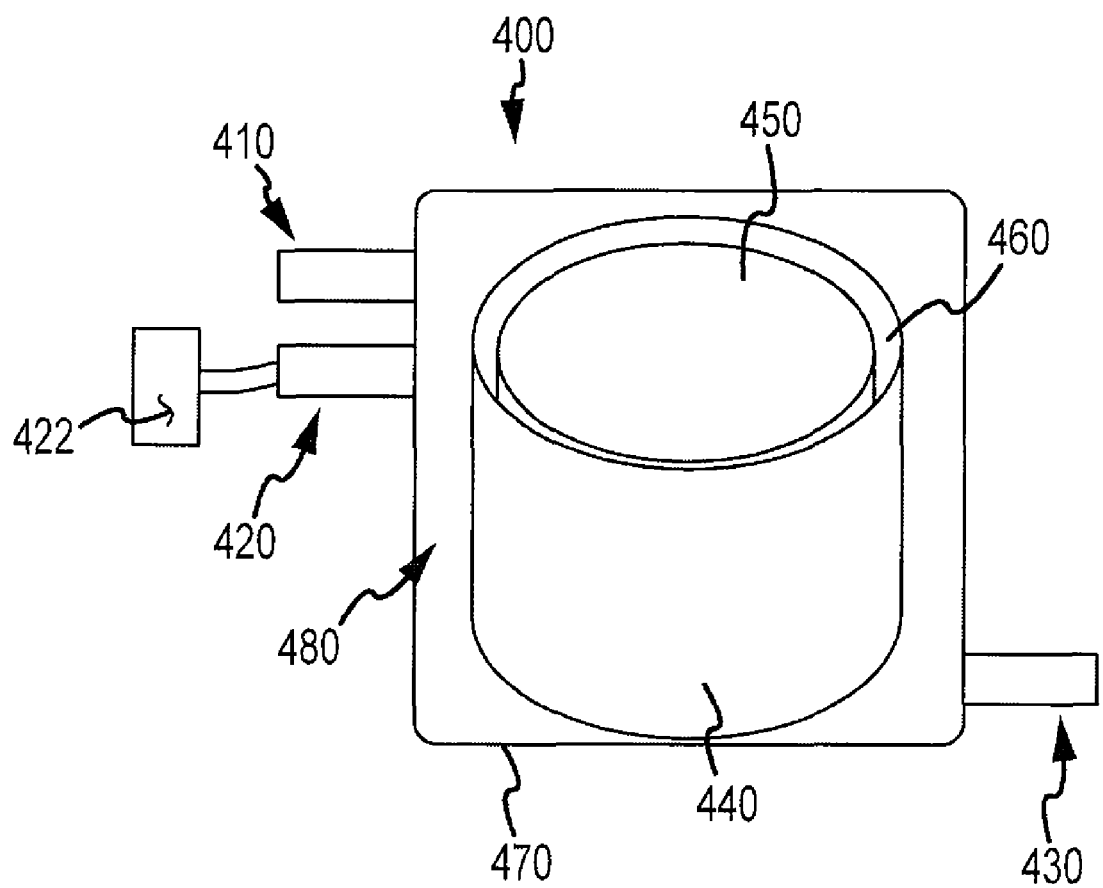
FIG. 4 shows an agitator according to embodiments of the present invention.

FIG. 4 illustrates an agitator 400 of a culture system according to embodiments of the invention. Agitator 400 includes a first input port 410 for receiving materials from a harvest zone of a photobioreactor, a second input port 420 for receiving materials for supplementing an algae growth media, and a first output port 430 for transmitting materials to an aggregator. Agitator 400 further includes a cavitation means 480, such as a housing 440 and a rotor 450, within an agitator body 470. As shown here, both rotor 450 and housing 440 are cylindrical in shape, and rotor 450 is disposed at least partially within housing 440 in concentric arrangement. A space 460 is present between rotor 450 and housing 440. In use, algae culture and media from a photobioreactor can be transmitted through input port 410 into agitator body 470. As relative rotational movement is generated between rotor 450 and housing 440, algae present in space 460 is lysed due to the resulting cavitation. The cell walls of the algae are broken, and algal oil or lipids are released from the algae into suspension. Thus, the cavitation, or sonic disruption, shreds the outer membrane of the algae.

In some embodiments, carbon dioxide and other gases or nutrients can be introduced from a source 422 into agitator body 470 via second input port 420. When the cavitation means 480 is activated, these gases or nutrients can be dissolved or otherwise incorporated into the media. Suitable cavitation means include cavitation wheels, hydrodynamic wheels, and the like. Any of a variety of supplemental materials may be introduced or dissolved into the media, including carbon dioxide, nitrogen (e.g. ammonium nitrate), phosphate, and the like. Carbon dioxide may be generated as a product of thermal biomass gasification in a wood gas generator, a downdraft gasifier, or the like. For example, wood can be gasified to produce wood gas, which is then burned directly in a spark ignition engine to produce electricity with a carbon dioxide exhaust. In another embodiment, wood gas can be treated with a steam process to produce liquid methanol, which can either be burned directly in a spark ignition engine or cracked to produce hydrogen and carbon dioxide. In some embodiments, carbon dioxide is purchased from a commercial supplier. It will be appreciated that systems and methods according to the present invention are well suited for carbon fixation or sequestration.

Hence, embodiments of the present invention provide for the ability to finely control or adjust the amount of nutrients, gasses, and other materials that are introduced into the media during agitation. Combined with the light control and temperature control aspects previously discussed, these culture systems are well suited for use in any of a variety of geographical climates and microclimates, where algae growing conditions may benefit from careful monitoring, adjustment, and optimization.

Figure 5:
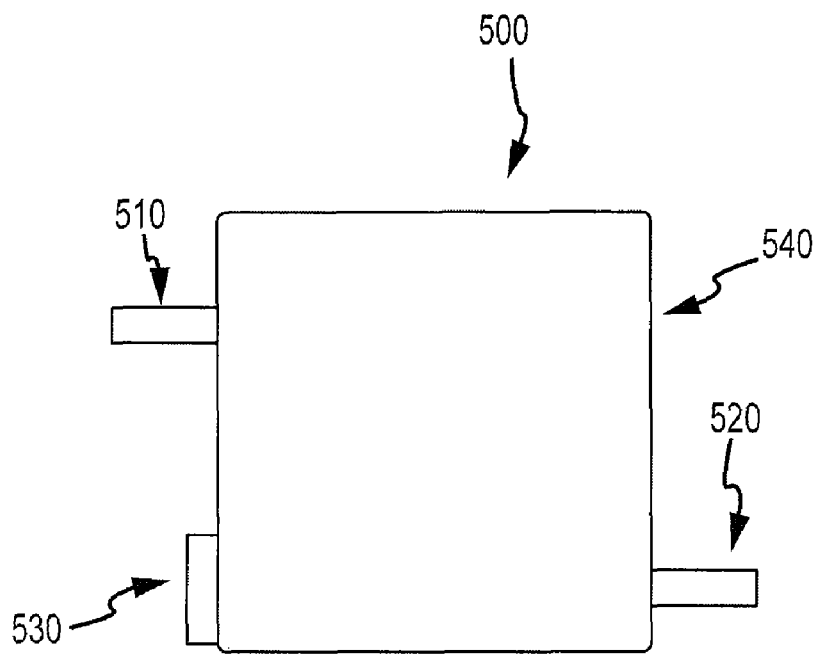
FIGS. 5 and 5A-5D show an aggregator according to embodiments of the present invention.
Figures 5A, 5B, 5C:
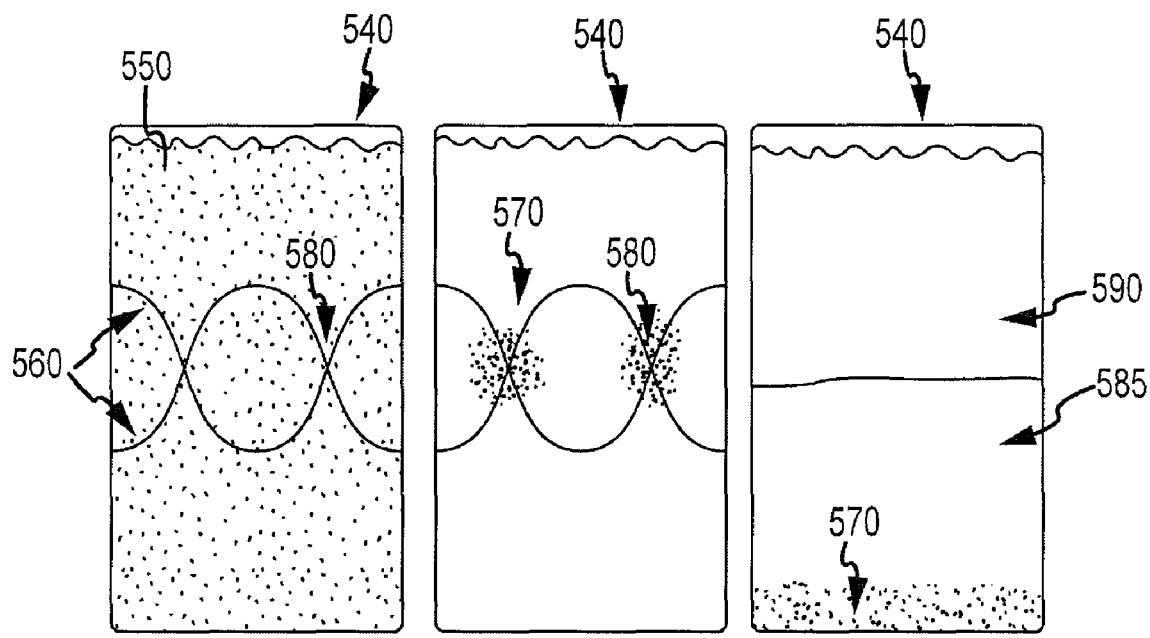
Figure 5D:
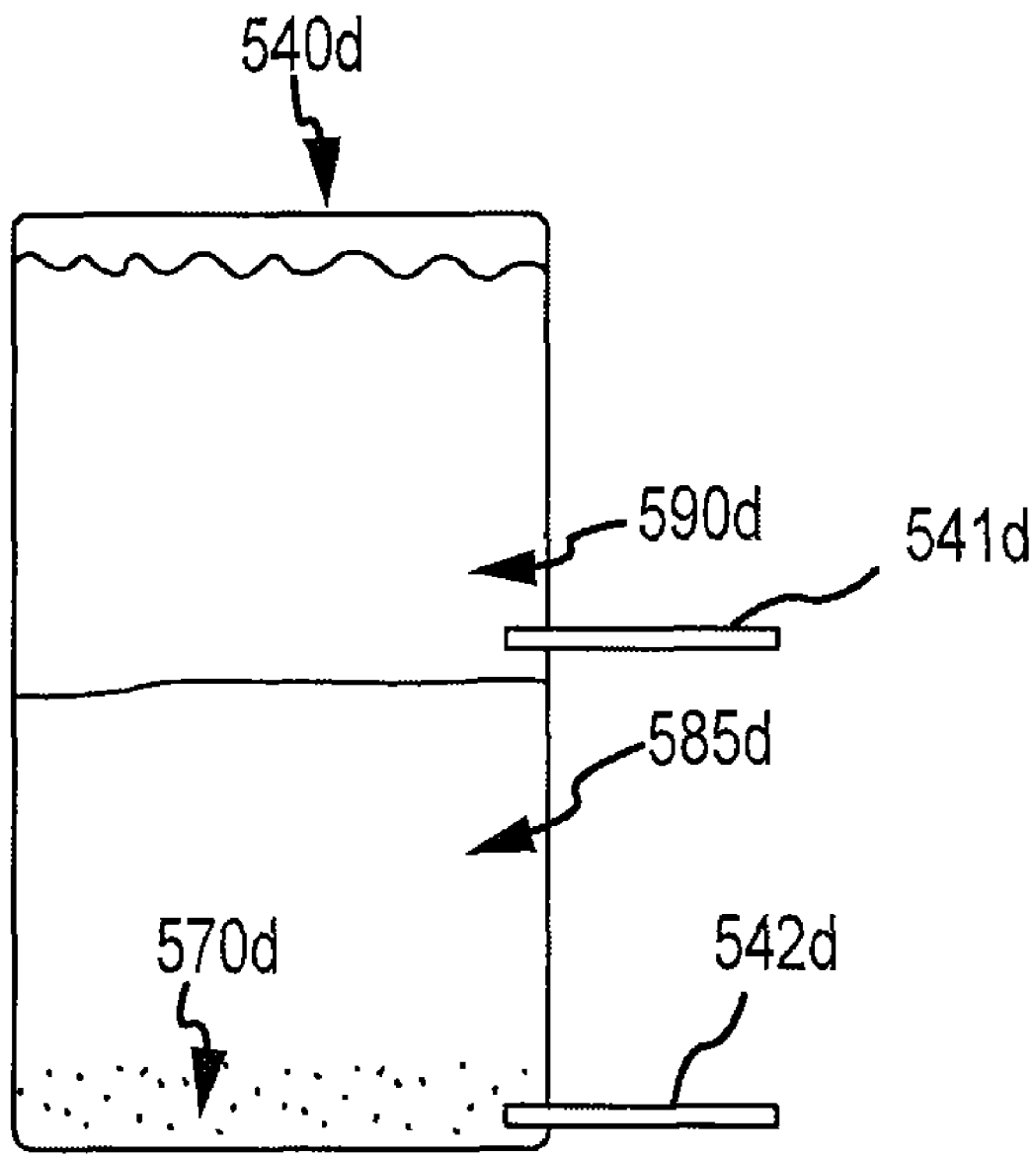

FIG. 5 shows an aggregator 500 of a culture system according to embodiments of the present invention. Aggregator 500 can be configured to facilitate the separation of a biofuel from a microalgae biomass. Aggregator 500 includes a first input port 510 for receiving material from an agitator, a first output port 520 for transmitting material to a photobioreactor, an ultrasonic generator 530, and an aggregation tank 540. In use, a lysed algae culture from an agitator is received into aggregation or flocculation tank via first input port 520. The lysed algae culture typically includes amounts of oil or lipids, water, and algae lysate or pulp. The aggregator acts to agglomerate algae pulp and to separate out components into layers or zones within aggregation tank 540. In some embodiments, aggregation tank 540 is shaped like an onion. Although such settlement or separation may occur naturally or as a result of gravitational forces alone, the application of ultrasound can expedite the settlement process, and can reduce amount of storage needed for a culture system. FIGS. 5A-5C show a time course sequence of an aggregation process. As depicted in FIG. 5A, flocculation tank 540 contains a homogenous mixture 550 of materials received from an agitator. The mixture can include oil, water, and algae pulp particulates. A standing wave 560 can be generated by a standing sonic wave generator. Upon application of standing wave 540, algae pulp particulates 570 aggregate at pressure nodes 580 in the ultrasonic field in a flocculation step, as shown in FIG. 5B. Upon sedimentation, pulp particulates 570 settle to the bottom of flocculation tank 540, and oil 590 and water 585 components separate. The algal oil 590 can then be easily removed from the tank, thus providing an effective and efficient approach for extracting an algal oil from an algae culture. According to the embodiment illustrated in FIG. 5D, a flocculation or aggregation tank 540d may have a first outlet passage 541d disposed toward a top portion of the tank, and a second outlet passage 542d disposed toward a bottom portion of the aggregation tank. In use, after algal oil 590d and pulp 570d are separated from water or media, pulp can settle toward the bottom of the tank, separate from the algal oil which rises toward the top of the tank. It is possible to remove the algal oil through the first passage disposed toward a top portion of the aggregation tank, and also remove the pulp through the second passage disposed toward a bottom portion of the aggregation tank. Some exemplary embodiments include transferring a volume that includes at least a portion of the suspension remaining in the aggregation tank to the agitator. This volume of suspension may include media, water, or the like. Such methods can include infusing the volume with carbon dioxide and nutrients via a cavitation process provided by the agitator.

Algal oil retrieved from an aggregator can be processed into biodiesel. In some embodiments, this process involves the chemical conversion of algal oil to its corresponding fatty ester via transesterification. In an exemplary transesterification process, using sodium ethanolate or sodium hydroxide as a catalyst, ethanol or methanol can be reacted with algal oil to produce biodiesel and glycerol. Biodiesel engines are often more efficient than gasoline engines. The culture system described herein provides a sustainable, recyclable closed system that avoids the problems associated with contamination, such as the introduction of algae strains from the outside environment.

Embodiments of the invention have now been described in detail. However, it will be appreciated that the invention may be carried out in ways other than those illustrated in the aforesaid discussion, and that certain changes and modifications may be practiced within the scope of the appended claims. Accordingly, the scope of this invention is not intended to be limited by those specific examples, but rather is to be accorded the scope represented in the following claims.

What is claimed is:

1. A method for illuminating a fluid cultivation medium containing an algae, comprising:
   concentrating a stream of light;
   transmitting the stream of light to an edge of an edge-lit sheet, the edge-lit sheet having a first surface, a second surface opposite the first surface, and reflector particles embedded within the sheet between the first surface and the second surface;
   transmitting the stream of light through the edge and into the edge-lit sheet within toward the embedded reflector particles so that the stream of sunlight is reflected by the embedded reflector particles;
   radiating the stream of light reflected by the embedded reflector particles through either the first surface or the second surface of the edge-lit sheet illuminator, wherein the surface through which the reflected light is radiated is in contact with the fluid cultivation medium; and
   illuminating the fluid cultivation medium containing the algae with the stream of light that is reflected by the embedded reflector particles and radiated through the first surface or the second surface.

2. The method of claim 1, wherein the stream of light is concentrated with a light concentrator having an aperture, and the stream of light is transmitted through the aperture of the light concentrator to the edge of the edge-lit sheet illuminator.

3. The method of claim 1, wherein the stream of light is concentrated with a parabolic concentrator.

4. The method of claim 1, wherein the stream of light is concentrated with a compound parabolic concentrator.

5. A photobioreactor for growing a microalgae biomass, comprising:
   a cultivation zone configured to contain a liquid culture medium and facilitate growth of the microalgae biomass; and
   a light concentrator mounted above the cultivation zone, the light concentrator having a light concentration surface that concentrates a stream of light and directs the stream of sunlight toward an illuminator,
   wherein the illuminator comprises an edge-lit sheet having an edge that receives and transmits the directed stream of light, a first surface, a second surface opposite the first surface, and reflector particles embedded within the sheet disposed between the first surface and the second surface, the embedded reflector particles positioned to reflect the transmitted stream of light, toward through the first surface or the second surface of the edge-lit sheet, the reflected light radiating from the from the first surface of the second surface so as to illuminate the microalgae biomass:
   wherein the surface through which the reflected light is radiated is in contact with the liquid culture medium.

6. The photobioreactor of claim 5, wherein the light concentrator comprises an aperture, and the light concentration surface comprises a parabolic shape.

7. The photobioreactor of claim 5, further comprising a cleaning element that runs along the first surface or the second surface of the illuminator and that is buoyed by the liquid culture medium.

8. The photobioreactor of claim 7, wherein the cleaning element comprises a brushing apparatus or a scraping apparatus.

9. The photobioreactor of claim 5, wherein the light concentrator comprises a compound parabolic concentrator.

10. The photobioreactor of claim 5, further comprising a collection zone having a rectangular configuration with a first and second pair of opposite sidewalls, and has a total volume sufficient to harvest at least half of the volume of the cultivation zone at periodic intervals.

11. The photobioreactor of claim 5, further comprising a zone for recovering heat from the cultivation zone, and cooling the same.

12. A culture unit for cultivating microalgae, comprising:
   a cultivation zone configured to contain a liquid culture medium and facilitate growth of the microalgae;
   a light concentrator mounted above the cultivation zone, the light concentrator having a light concentration surface that concentrates a stream of light and directs the sunlight of light toward an edge of an edge-lit sheet, the edge-lit sheet having a first surface, a second surface opposite the first surface, and reflector particles embedded within the sheet between the first surface and the second surface, such that the cultivation zone is defined at least in part by the first surface or the second surface;
   a collection zone in fluid communication with the cultivation zone;
   a hydrodynamic separation zone in fluid communication with the cultivation zone, wherein the hydrodynamic separation zone is configured to break a cell wall of the microalgae to allow algal oil to release from the algae into a suspension;
   a flocculation tank in fluid communication with the hydrodynamic separation zone, such that the suspension comprising the released algal oil can be transferred from the hydrodynamic separation zone to the flocculation tank; and
   a standing sonic wave generator configured to create a standing sonic wave within the flocculation tank;
   wherein the hydrodynamic separation zone comprises a cavitation mixer having a rotor and a housing, wherein the rotor is disposed at least partially within the housing in a concentric arrangement.

13. The culture unit of claim 12, wherein the cavitation mixer is configured to separate at least a portion of the microalgae and liquid culture medium into a solid phase containing a solid component of the microalgae and at least one liquid phase.

14. The culture unit of claim 12, further comprising an oxygen container in fluid communication with the cultivation zone via a conduit.

* * * * *

UNITED STATES PATENT AND TRADEMARK OFFICE
CERTIFICATE OF CORRECTION

PATENT NO. : 7,950,181 B2  Page 1 of 1
APPLICATION NO. : 12/015638
DATED : May 31, 2011
INVENTOR(S) : Joe McCall It is certified that error appears in the above-identified patent and that said Letters Patent is hereby corrected as shown below:

Claim 1, column 17, line 43, please delete "within".

Claim 1, column 17, line 44, please delete "sunlight" and insert --light--.

Claim 1, column 17, line 48, please delete "illuminator".

Claim 2, column 17, line 58, please delete "illuminator".

Claim 5, column 18, line 9, please delete "disposed".

Claim 5, column 18, line 11, please delete "through".

Claim 5, column 18, line 15, please delete "biomass:" and insert --biomass,--.

Claim 12, column 18, line 44, please delete "sunlight" and insert --stream--.

Signed and Sealed this
Twenty-sixth Day of July, 2011

David J. Kappos
*Director of the United States Patent and Trademark Office*